US010253032B2

(12) United States Patent
Lowe, III et al.

(10) Patent No.: US 10,253,032 B2
(45) Date of Patent: *Apr. 9, 2019

(54) SPIRO-LACTAM NMDA RECEPTOR MODULATORS AND USES THEREOF

(71) Applicant: Aptinyx Inc., Evanston, IL (US)

(72) Inventors: John A. Lowe, III, Stonington, CT (US); M. Amin Khan, Evanston, IL (US)

(73) Assignee: Aptinyx Inc., Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/653,738

(22) Filed: Jul. 19, 2017

(65) Prior Publication Data

US 2018/0155354 A1   Jun. 7, 2018

Related U.S. Application Data

(63) Continuation of application No. 14/764,419, filed as application No. PCT/US2014/013626 on Jan. 29, 2014, now Pat. No. 9,738,650.

(60) Provisional application No. 61/757,939, filed on Jan. 29, 2013.

(51) Int. Cl.
C07D 487/10   (2006.01)

(52) U.S. Cl.
CPC ................... C07D 487/10 (2013.01)

(58) Field of Classification Search
CPC .................................................. C07D 487/10
See application file for complete search history.

(56) References Cited

U.S. PATENT DOCUMENTS

| | | | |
|---|---|---|---|
| 4,904,681 A | 2/1990 | Cordi et al. |
| 4,959,493 A | 9/1990 | Ohfume et al. |
| 5,061,721 A | 10/1991 | Cordi et al. |
| 5,086,072 A | 2/1992 | Trullas et al. |
| 5,166,136 A | 11/1992 | Ward et al. |
| 5,168,103 A | 12/1992 | Kinney et al. |
| 5,350,769 A | 9/1994 | Kasai et al. |
| 5,523,323 A | 6/1996 | Maccecchini |
| 5,605,911 A | 2/1997 | Olney et al. |
| 5,648,259 A | 7/1997 | Mallet et al. |
| 5,741,778 A | 4/1998 | Martin et al. |
| 5,763,393 A | 6/1998 | Moskal et al. |
| 5,804,550 A | 9/1998 | Bourguignon |
| 5,902,815 A | 5/1999 | Olney et al. |
| 5,952,389 A | 9/1999 | Fogel |
| 5,959,075 A | 9/1999 | Lok et al. |
| 6,007,841 A | 12/1999 | Caruso |
| 6,025,471 A | 2/2000 | Deghenghi |
| 6,107,271 A | 8/2000 | Moskal et al. |
| 6,147,230 A | 11/2000 | Shimamoto et al. |
| 6,197,820 B1 | 3/2001 | Sontheimer et al. |
| 6,521,414 B2 | 2/2003 | Melcher et al. |
| 6,541,453 B2 | 4/2003 | Oldham et al. |
| 6,635,270 B2 | 10/2003 | Hong et al. |
| 6,667,317 B2 | 12/2003 | Chenard et al. |
| 6,821,985 B2 | 11/2004 | Chenard et al. |
| 6,828,318 B2 | 12/2004 | Snape et al. |
| 7,273,889 B2 | 9/2007 | Mermelstein et al. |
| 7,884,080 B2 | 2/2011 | Aslanian et al. |
| 8,492,340 B2 | 7/2013 | Moskal |
| 9,504,670 B2 | 11/2016 | Lowe, III et al. |
| 9,512,133 B2 | 12/2016 | Khan et al. |
| 9,512,134 B2 | 12/2016 | Lowe, III et al. |
| 9,579,304 B2 | 2/2017 | Lowe, III et al. |
| 9,708,335 B2 | 7/2017 | Lowe, III et al. |
| 9,738,650 B2 | 8/2017 | Lowe, III et al. |
| 9,758,525 B2 | 9/2017 | Lowe, III et al. |
| 9,802,946 B2 | 10/2017 | Khan et al. |
| 9,828,384 B2 | 11/2017 | Lowe, III et al. |
| 2002/0103335 A1 | 8/2002 | Oldham et al. |
| 2003/0022253 A1 | 1/2003 | Moskal |
| 2003/0064921 A1 | 4/2003 | Millhauser et al. |
| 2003/0175734 A1 | 9/2003 | Kroes et al. |
| 2005/0037433 A1 | 2/2005 | Nakanishi et al. |
| 2005/0118286 A1 | 6/2005 | Suffin et al. |
| 2006/0063707 A1 | 3/2006 | Baudry et al. |
| 2006/0241046 A1 | 10/2006 | Olivera et al. |
| 2007/0087404 A1 | 4/2007 | Stahl et al. |
| 2007/0208001 A1 | 9/2007 | Zhuo et al. |
| 2009/0221544 A1 | 9/2009 | Stein et al. |
| 2010/0102616 A1 | 4/2010 | Yamasaki et al. |
| 2011/0306586 A1 | 12/2011 | Khan et al. |
| 2012/0295852 A1 | 11/2012 | Moskal |

(Continued)

FOREIGN PATENT DOCUMENTS

CN   101066945 A   11/2007
CN   101125817 A   2/2008

(Continued)

OTHER PUBLICATIONS

Abbott AV et al., 'The Formalin Test: Scoring Properties of the First and Second Phases of the Pain Response in Rats,' Pain, Jan. 1995 (Jan. 1995), 60(1):91-102.

Abramets, II, 'Neurophysiological and Neurochemical Aspects of the Effects of Antidepressants and Mood Stabilizers,' Neurophysiol, Jan. 2008 (Jan. 2008), 40(1):64-78.

Alonso E et al., 'Spiro-Beta-Lactams as Beta-Turn Mimetics. Design, Synthesis, and NMR Conformational Analysis,' J Org Chem, Sep. 21, 2001 (Sep. 21, 2001), 66(19):6333-8.

Anonymous, Database Accession No. 1031928-30-9, Database Registry [Online] Chemical Abstracts Service, Columbus, Ohio, US; Jul. 1, 2008 (Jul. 1, 2008), XP002668992.

Anonymous, Database Accession No. 1053605-89-2, Database Registry [Online] Chemical Abstracts Service, Columbus, Ohio, US; Sep. 28, 2008 (Sep. 28, 2008), XP002668993.

(Continued)

Primary Examiner — Laura L Stockton
(74) Attorney, Agent, or Firm — Goodwin Procter LLP

(57) ABSTRACT

Disclosed are compounds having enhanced potency in the modulation of NMDA receptor activity. Such compounds are contemplated for use in the treatment of conditions such as depression and related disorders. Orally available formulations and other pharmaceutically acceptable delivery forms of the compounds, including intravenous formulations, are also disclosed.

20 Claims, No Drawings

(56) References Cited

U.S. PATENT DOCUMENTS

| | | |
|---|---|---|
| 2013/0005662 A1 | 1/2013 | Moskal |
| 2013/0035292 A1 | 2/2013 | Moskal et al. |
| 2013/0053325 A1 | 2/2013 | Moskal et al. |
| 2013/0310323 A1 | 11/2013 | Moskal |
| 2013/0316954 A1 | 11/2013 | Moskal |
| 2014/0107037 A1 | 4/2014 | Moskal |
| 2015/0051262 A1 | 2/2015 | Khan et al. |
| 2015/0105364 A1 | 4/2015 | Khan et al. |
| 2015/0336969 A1 | 11/2015 | Khan et al. |
| 2015/0368252 A1 | 12/2015 | Lowe, III et al. |
| 2015/0368253 A1 | 12/2015 | Lowe, III et al. |
| 2015/0368254 A1 | 12/2015 | Lowe, III et al. |
| 2015/0376195 A1 | 12/2015 | Lowe, III et al. |
| 2017/0231956 A1 | 8/2017 | Lowe, III et al. |

FOREIGN PATENT DOCUMENTS

| | | |
|---|---|---|
| CN | 103974712 A | 8/2014 |
| CN | 104321071 A | 1/2015 |
| EP | 2542254 A1 | 1/2013 |
| EP | 2771021 | 5/2013 |
| JP | 2013519683 A | 5/2013 |
| JP | 2014520072 A | 8/2014 |
| RU | 2039035 C1 | 7/1995 |
| WO | WO-1996/032105 A1 | 10/1996 |
| WO | WO-1997/043306 A1 | 11/1997 |
| WO | WO-1999/024584 A1 | 5/1999 |
| WO | WO-1999/051985 A1 | 10/1999 |
| WO | WO-2000/028090 A2 | 5/2000 |
| WO | WO-2001/36685 A2 | 5/2001 |
| WO | WO-2001/96606 A2 | 12/2001 |
| WO | WO-2001/98367 A2 | 12/2001 |
| WO | WO-2002/47535 A2 | 6/2002 |
| WO | WO-2002/072609 A2 | 9/2002 |
| WO | WO-2003/010540 A1 | 2/2003 |
| WO | WO-2004/005293 A2 | 1/2004 |
| WO | WO-2005/020973 A2 | 3/2005 |
| WO | WO-2005/035535 A1 | 4/2005 |
| WO | WO-2007/103719 A2 | 9/2007 |
| WO | WO-2009/039390 A2 | 3/2009 |
| WO | WO-2009/105718 A1 | 8/2009 |
| WO | WO-2010/015545 A1 | 2/2010 |
| WO | WO-2010/033757 A1 | 3/2010 |
| WO | WO-2010/065709 A2 | 6/2010 |
| WO | WO-2010/102616 A1 | 9/2010 |
| WO | WO-2011/003064 A2 | 1/2011 |
| WO | WO-2011/044089 A2 | 4/2011 |
| WO | WO-2011/100585 A1 | 8/2011 |
| WO | WO-2012/149389 A2 | 11/2012 |
| WO | WO-2013/001448 A1 | 1/2013 |
| WO | WO-2013/063120 A2 | 5/2013 |
| WO | WO-2014/011590 A2 | 1/2014 |
| WO | WO-2014/120783 A1 | 8/2014 |
| WO | WO-2014/120784 A1 | 8/2014 |
| WO | WO-2014/120786 A1 | 8/2014 |
| WO | WO-2014/120800 A1 | 8/2014 |

OTHER PUBLICATIONS

Anonymous, NCBI Submission NM 000149, 'Homo sapiens Fucosyltransferase 3 (galactoside 3(4)-L-fucosyltransferase, Lewis Blood Group)(FUT3), Transcript Variant 1, mRNA,' 1990 (1990), Retrieved from the internet; «URL:http://www.ncbi.nlm.nih.gov/nuccore/148277008», pp. 1-5.

Anonymous, NCBI Submission NM 001276, 'Homo sapiens Chitinase 3-like 1 (cartilage glycoprotein-39)(CH13L1), mRNA,' 1989 (1989), Retrieved from the internet; <URL:http://www.ncbi.nlm.nih.gov/nuccore/144226250>, pp. 1-5.

Anonymous, NCBI Submission NM_030979.1, 'Homo sapiens poly(A) Binding Protein, Cytoplasmic 3 (PABPC3), mRNA,' 2003 (2003), Retrieved from the internet; <URL:http://www.ncbi.nlm.nih.gov/nuccore/13569957>, pp. 1.

Anonymous, NCBI Submission NM_173216, 'Homo sapiens ST6 beta-galactosamide alpha-2,6-sialyltransferase 1 (ST6GAL1), transcript variant 1, mRNA,' 1989 (1989), Retrieved from the internet; <URL:http://www.ncbi.nlm.nih.gov/nuccore/27765090>, pp. 1-5.

Bennett GJ and Xie Y-K, 'A Peripheral Mononeuropathy in Rat That Produces Disorders of Pain Sensation Like Those Seen in Man,' Pain, Apr. 1988 (Apr. 1988), 33(1):87-107.

Bittermann H and Gmeiner P, 'Chirospecific Synthesis of Spirocyclic beta-Lactams and Their Characterization as Potent Type II beta-Turn Inducing Peptide Mimetics,' J Org Chem, Jan. 6, 2006 (Jan. 6, 2006), 71(1):97-102.

Bittermann H et al., 'A Highly Practical RCM Approach Towards a Molecular Building Kit of Spirocyclic Reverse Turn Mimics,' Chem Eur J, Aug. 16, 2006 (Aug. 16, 2006), 12(24):6315-22.

Burch RM et al., 'GLYX-13, An NMDA Receptor Glycine Site Functional Partial Agonist, Does Not Elicit Psychotomimetic Side Effects in Normal Human Volunteers at Doses Expected to be Therapeutic in Treatment-Resistant Major Depressive Disorder,' NCDEU, Jun. 16, 2010 (Jun. 16, 2010), Naurex, Inc., Evanston, IL (Publ), pp. 1 (Poster #unknown).

Burgdorf JS et al., 'Neurobiology of 50-kHz Ultrasonic Vocalizations in Rats: Electrode, Lesion, and Pharmacology Studies,' Behav Brain Res, Mar. 19, 2007 (Mar. 19, 2007) (ePub), 182(2):274-83.

Burgdorf JS et al., 'The Antidepressant and Anxiolytic Properties of GLYX-13: A Novel NMDA Receptor Glycine Site Functional Partial Agonist,' *ACNP 2010 Meeting*, Dec. 6, 2010 (Dec. 6, 2010),pp. 1 (Poster #198) .

Burgdorf JS et al., 'The Effects of Selective Breeding for Differential Rates of 50-kHz Ultrasonic Vocalizations on Emotional Behavior in Rats,' Dev Psychobiol, Jan. 2009 (Jan. 2009), 51(1):34-46.

Burgdorf JS et al., 'The N-Methyl-D-Aspartate Receptor Modulator GLYX-13 Enhances Learning and Memory, in Young Adult and Learning Impaired Aging Rats,' Neurobiol Aging, May 14, 2009 (May 14, 2009) (ePub), 32(4):698-706.

Burgdorf JS et al., 'Uncovering the Molecular Basis of Positive Affect Using Rough-and-Tumble Play in Rats: A Role for the NMDA Receptor and Implications for Depression,' Neuroscience, Jul. 14, 2010, (Jul. 14, 2010) (ePub), 168(3):769-77.

Burgdorf JS et al., 'Uncovering the Molecular Basis of Positive Affect Using Rough-and-Tumble Play in Rats: A Role for the NMDA Receptor and Implications for Depression,' Neuroscience 38th Annual Meeting, Washington DC, Nov. 17, 2008 (Nov. 17, 2008), pp. 1-2 (Poster #393.1/UU11) [Electronically available Sep. 2008].

Careri M et al., 'Pentcopper(II) 12-Metallacrown-4 Complexes with alpha- and beta-Aminohydroxamic Acids in Aqueous Solution: A Reinvestigation,' J Inorg Chem, Jan. 15, 2003 (Jan. 15, 2003), 93(3-4)1 74-80.

Coates C et al., 'Product Class 9: Beta-Lactams,' *Science of Synthesis*, Georg Thieme Verlag KG, Stuttgart, DE (Pub), 2000 (2000), 21:609-46

Cremonesi G et al., 'Enantiomerically Pure Polyheterocyclic Spiro-beta-Lactams from trans-4-Hydroxy-L-proline,' J Org Chem, Mar. 19, 2010 (Mar. 19, 2010), 75(6):2010-7.

Dalla Croce P and La Rosa C, 'Stereoselective Synthesis of N-Phenylsulfonyl Substituted Spiro-beta-Lactams,' Tetrahedron: Asymmetry, Mar. 26, 1999 (Mar. 26, 1999), 10(6):1193-9.

Dalla Croce P et al., 'Reaction of Mesoionic Compounds Deriving from Cyclic N-Acyl-alpha-amino Acids with N-(Phenylmethylene)benzenesulfonamide,' Tetrahedron, Jan. 1, 1999 (Jan. 1, 1999), 55(1):201-10.

Del Pozo C et al., 'Diastereo- and Enantioselective Synthesis of Novel beta-Lactam-Containing 1,4-Benzodiazepines Through a Ketene-Imine Cycloaddition Reaction,' Eur J Org Chem, Jan. 19, 2004 (Jan. 19, 2004), 2004(3):535-45.

Duman RS, 'Pathophysiology of Depression: The Concept of Synaptic Plasticity,' Eur Psychiatry, Jul. 2002 (Jul. 2002), 17(Suppl 3):306-10.

Erick M Carreira and Lisbet Kvaerno, Classics in Stereoselective Synthesis, (1st ed. 2009), Wiley-Vch Verlag GmbH & Co. KGaA, Weinham, DE (Publ), pp. 19-102 ISBN: 978-3-527-32452-1.

European Patent Office, Supplementary European Search Report (Form 1503) for EP 09 81 5233 (Fink D), completed at Munich DE on Feb. 8, 2012 (Feb. 8, 2012) pp. 1-3.

(56) References Cited

OTHER PUBLICATIONS

European Patent Office, Supplementary European Search Report (Form 1503) for EP 10 82 2514 (Fink D), completed at Munich DE on Feb. 1, 2013 (Feb. 1, 2013) pp. 1-2.
Forni A, 'Two Diastereoisomers of 2-(Benzenesulfonyl)-5-benzoyl-1-oxo-3-phenyl-2,5-diazaspiro[3.4]octan-7-yl acetate,' Acta Crystallographica Sec C: Crystal Structure Commun, Sep. 1998 (Sep. 1998), C54(9):1320-2.
Foster AC and Fagg GE, 'Neurobiology: Taking Apart NMDA Receptors,' Nature, Oct. 1, 1987 (Oct. 1, 1987), 329(6138):395-6.
Golik U, 'Synthesis of Malonimide Derivatives as Potential Penicillin Analogs,' J Heterocycl Chem, Feb. 1972 (Feb. 1972), 9(1):21-4.
Grigg R et al., 'X=Y-ZH Systems as Potential 1,3-Dipoles. Part 46. Cascade 1,3-Dipolar Cycloaddition Reactions of Cephalosporin Imines,' Tetrahedron, Nov. 1995 (Nov. 1995), 51(48):13347-56.
Haring R et al., 'Binding Studies and Photoaffinity Labeling Identify Two Classes of Phencyclidine Receptors in Rat Brain,' Biochemistry, Sep. 8, 1987 (Sep. 8, 1987), 26(18):5854-61.
Haring R et al., 'Glycine-Like Modulation of N-Methyl-D-Aspartate Receptors by a Monoclonal Antibody that Enhances Long-Term Potentiation,' J Neurochem, Jul. 1991 (Jul. 1991), 57(1):323-32.
Haring R et al., 'Identification of Polypeptides of the Phencyclidine Receptor of Rat Hippocampus by Photoaffinity Labeling with [H3]Azidophencyclidine,' Biochemistry, Feb. 11, 1986 (Feb. 11, 1986), 25(3):612-20.
Haring R et al., 'Multiple Mode of Binding of Phencyclidines: High Affinity Association Between Phencyclidine Receptors in Rat Brain and a Monovalent Ion-Sensitive Polypeptide,' Biochem Biophys Res Commun, Jan. 30, 1987 (Jan. 30, 1987), 142(2):501-10.
Holderbach R et al., 'Enhanced Long-Term Synaptic Depression in an Animal Model of Depression,' Biol Psychiatry, Dec. 4, 2006 (Dec. 4, 2006) (ePub), 62(1):92-100.
International Searching Authority, International Search Report (ISA/210) for Application No. PCT/US08/77045, (Young LW), completed on Mar. 28, 2009 (Mar. 28, 2009) and dated Apr. 29, 2009 (Apr. 29, 2009), pp. 1-3.
International Searching Authority, International Search Report (ISA/210) for Application No. PCT/US09/57401, (Young LW), completed Dec. 6, 2009 (Dec. 6, 2009) and dated Dec. 24, 2009 (Dec. 24, 2009), pp. 1-2.
International Searching Authority, International Search Report (ISA/210) for Application No. PCT/US09/66536, (Kang YJ), completed Aug. 9, 2010 (Aug. 9, 2010) and dated Aug. 9, 2010 (Aug. 9, 2010), pp. 1-5.
International Searching Authority, International Search Report (ISA/210) for Application No. PCT/US2014/013619, (Wolf C), completed Mar. 6, 2014 (Mar. 6, 2014) and dated Mar. 20, 2014 (Mar. 20, 2014), pp. 1-3.
International Searching Authority, International Search Report (ISA/210) for Application No. PCT/US2014/013621, (Wolf C), completed Feb. 27, 2014 (Feb. 27, 2014) and dated Mar. 13, 2014 (Mar. 13, 2014), pp. 1-2.
International Searching Authority, International Search Report (ISA/210) for Application No. PCT/US2014/013623, (Wolf C), completed Mar. 3, 2014 (Mar. 3, 2014) and dated Mar. 13, 2014 (Mar. 13, 2014), pp. 1-3.
International Searching Authority, International Search Report (ISA/210) for Application No. PCT/US2014/013626, (Rudolf M), completed Mar. 10, 2014 (Mar. 10, 2014) and dated Mar. 18, 2014 (Mar. 18, 2014), pp. 1-4.
International Searching Authority, International Search Report (ISA/210) for Application No. PCT/US2014/013639, (Wolf C), completed Feb. 28, 2014 (Feb. 28, 2014) and dated Mar. 13, 2014 (Mar. 13, 2014), pp. 1-3.
International Searching Authority, Written Opinion of Application No. PCT/US2008/077045 (ISA/237), (Young LW), completed Mar. 28, 2009 (Mar. 28, 2009) and dated Mar. 24, 2010 (Mar. 24, 2010), pp. 1-8.
International Searching Authority, Written Opinion of Application No. PCT/US2009/057401 (ISA/237), (Young LW), completed Dec. 6, 2009 (Dec. 6, 2009) and dated Mar. 22, 2011 (Mar. 22, 2011), pp. 1-6.
International Searching Authority, Written Opinion of Application No. PCT/US2009/066536 (ISA/237), (Kang YJ), completed Aug. 9, 2010 (Aug. 9, 2010) and dated Jun. 7, 2011 (Jun. 7, 2011), pp. 1-8.
International Searching Authority, Written Opinion of Application No. PCT/US2014/013619 (ISA/237), (Wolf C), completed Mar. 6, 2014 (Mar. 6, 2014) and dated Aug. 4, 2015 (Aug. 4, 2015), pp. 1-4.
International Searching Authority, Written Opinion of Application No. PCT/US2014/013621 (ISA/237), (Wolf C), completed Feb. 27, 2014 (Feb. 27, 2014) and dated Aug. 4, 2015 (Aug. 4, 2015), pp. 1-6.
International Searching Authority, Written Opinion of Application No. PCT/US2014/013623 (ISA/237), (Wolf C), completed Mar. 3, 2014 (Mar. 3, 2014) and dated Aug. 4, 2015 (Aug. 4, 2015), pp. 1-4.
International Searching Authority, Written Opinion of Application No. PCT/US2014/013626 (ISA/237), (Rudolf M, completed Mar. 10, 2014 (Mar. 10, 2014) and dated Aug. 4, 2015 (Aug. 4, 2015), pp. 1-6.
International Searching Authority, Written Opinion of Application No. PCT/US2014/013639 (ISA/237), (Wolf C), completed Feb. 28, 2014 (Feb. 28, 2014) and dated Aug. 4, 2015 (Aug. 4, 2015), pp. 1-4.
Johnson JA et al., 'The Preparation of a Double Metallahelicate Containing 28 Copper Atoms,' Angew Chem Int Ed Engl, Feb. 3, 2003 (Feb. 3, 2003), 42(5):546-9.
Johnson KM and Jones SM, 'Neuropharmacolgy of Phencyclidine: Basic Mechanisms and Therapeutic Potential,' Annu Rev Pharmacol Toxicol, 1990 (1990), 30:707-50.
Khasanov AB et al., 'Novel Asymmetric Approach to Proline-Derived Spiro-beta-Lactams,' J Org Chem., Aug. 20, 2004 (Aug. 20, 2004), 69(17):5766-9.
Kloog Y et al., 'Kinetic Characterization of the Phencyclidine-N-Methyl-d-asparate Receptor Interaction: Evidence for a Steric Blockade of the Channel,' Biochemistry, Feb. 9, 1988 (Feb. 9, 1988), 27(3):843-8.
Kloog Y et al., 'Mode of Binding of [3H]dibenzocycloalkenimine (MK-801) to the N-methyl-D-Aspartate (NMDA) Receptor and its Therapeutic Implication,' FEBS Letts, Mar. 28, 1988 (Mar. 28, 1988), 230(1-2):167-70.
Koller M and Urwyler S, 'Novel N-Methyl-D-aspartate Receptor Antagonists: A Review of Compounds Patented Since 2006,' Expert Opin Ther Pat, Nov. 8, 2010 (Nov. 8, 2010) (epub), 20(12):1683-702.
Kroes RA et al., 'Development of a Novel Glycobiologic Therapy for Glioblastoma,' Neuro-oncol, Oct. 2006 (Oct. 2006), 8(4):397-8, (Abstract #CB-14).
Kroes RA et al., 'Development of a Novel Glycobiology-Based Therapeutic for Glioblastoma,' J Neurochem, Nov. 10, 2006 (Nov. 10, 2006), 99(Suppl. 1):17 (Abstract #50).
Krystall JH et al., 'NMDA Agonists and Antagonists as Probes of Glutamatergic Dysfunction and Pharmacotherapies in Neuropsychiatric Disorders,' Harvard Rev Psychiatry, Sep.-Oct. 1999 (Sep.-Oct. 1999), 7(3):125-43.
Leander JD et al., 'Lack of Ketamine-Like Discriminative Effects of GLYX-13: A Novel NMDA Receptor Glycine Site Functional Partial Agonist with Antidepressant-Like Preclinical Effects,' ACNP 49th Annual Meeting, Dec. 2010 (Dec. 2010), Miami Beach, FL, Naurex, Inc., Evanston, IL (Pub) (Poster #218).
Li G-Q et al., 'N-Heterocyclic Carbene Catalyzed Ring Expansion of 4-Formyl-beta-lactams: Synthesis of Succinimide Derivatives,' Org Lett, Aug. 9, 2007 (Aug. 9, 2007) (ePub), 9(18):3519-21.
Lynch G et al., 'Synaptic Pasticity in Early Aging,' Ageing Res Rev, Aug. 28, 2006 (Aug. 28, 2006) (ePub), 5(3):255-80.
Macias A et al., 'Diastereoselective [2+2]-Cycloaddition Reactions of Unsymmetrical Cyclic Ketenes with Imines: Synthesis of Modified Prolines and Theoretical Study of the Reaction Mechanism,' J Org Chem, Oct. 1, 2004 (Oct. 1, 2004) Sep. 10, 2005 (Sep. 10, 2005)(ePub), 69(21):7004-12.
Macias A et al., 'Unusual Rearrangement of Spiro-beta-Lactams to 1,4-diazabicyclo[4,4,0]decanes and 1,4-diazabicyclo[4,3,0]nonanes.

(56) References Cited

OTHER PUBLICATIONS

Synthesis of Conformationally Restricted Sigma-Receptor Ligands,' Tetrahedron Lett, Jun. 2004 (Jun. 2004), 45(24):4657-60.

Marcias A et al., 'Synthesis of Enantiopure Pyrrolidine-Derived Peptidomimetics and Oligo-beta-Peptides via Nucleophilic Ring-Opening of beta-Lactams,' J Org Chem, Sep. 29, 2006 (Sep. 29, 2006), 71(20):7721-30.

Mayer ML and Miller RJ, 'Excitatory Amino Acid Receptors, Second Messengers and Regulation of Intracellular Ca2+ in Mammalian Neurons,' Trends Pharmacol Sci, Jun. 1990 (Jun. 1990), 11(6):254-60.

McLeod MN et al., 'Chromium Potentiation of Antidepressant Pharmacotherapy for Dysthymic Disorder in 5 Patients,' J Clin Psychiatry, Apr. 1999 (Apr. 1999), 60(4):237-40.

Mishra H et al., 'Three-Dimensional Quantitative Structure-Activity Relationship and Comparative Molecular Field Analysis of Dipeptide Hydroxamic Acid Helicobacter pylori Urease Inhibitors,' Antimicrob Agents Chemother, Aug. 2002 (Aug. 2002), 46(8):2613-8.

Monahan JB et al., 'D-Cycloserine, a Positive Modulator of the N-Methyl-d-Asparate Receptor, Enhances Performance of Learning in Rats,' Pharmacol Biochem Behav, Nov. 1989 (Nov. 1989), 34(3):649-53.

Moskal JR and Burgdorf JS, 'The Antidepressant and Anxiolytic Properties of GLYX-13: A Novel NMDA Receptor Glycine Site Functional Partial Agonist,' ACNP 29th Annual Meeting, Dec. 7, 2009 (Dec. 7, 2009), Hollywood, FL, Naurex, Inc. Evanston, IL (Pub) (Poster #059).

Moskal JR and Schaffner AE, 'Monoclonal Antibodies to the Dentate Gyrus: Immunocytochemical Characterization and Flow Cytometric Analysis of Hippocampal Neurons Bearing a Unique Cell-Surface Antigen,' J Neurosci, Jul. 1986 (Jul. 1986), 6(7):2045-53.

Moskal JR et al., 'A Novel Approach to Unlocking the Therapeutic Potential of the NMDA Receptor,' Vital Signs e-Magazine, Sep. 2010 (Sep. 2010), pp. 1-2.

Moskal JR et al., 'GLYX-13: A Monoclonal Antibody-Derived Peptide that Acts as an N-Methyl-D-Aspartate Receptor Modulator,' Neuropharmacol, Jul. 26, 2005 (Jul. 26, 2005) (ePub), 49(7):1077-87.

Moskal JR et al., 'The Use of Antibody Engineering to Create Novel Drugs that Target N-Methyl-D-Aspartate Receptors,' Curr Drug Targets, Sep. 2001 (Sep. 2001), 2(3):331-45.

Moskal JR, 'The Anti-depressant and Anxiolytic Properties of GLYX-13: A Glycine-site Functional Partial Agonist (GFPA), a Novel Mechanism for Modulating NMDA,' ACNP 48th Annual Meeting, Dec. 7, 2009 (Dec. 7, 2009), Hollywood, FL, pp. 1-2 (Abstract).

Myers SM and Johnson CP, 'Management of Children with Autism Spectrum Disorders,' Pediatrics, Oct. 29, 2007 (Oct. 29, 2007) (ePub), 120(5):1162-82.

Narahashi T et al., 'Mechanisms of Action of Cognitive Enhancers on Neuroreceptors,' Biol Pharm Bull, Nov. 2004 (Nov. 2004), 27(11):1701-6.

Overman LE and Osawa T, 'A Convenient Synthesis of 4-Unsubstituted beta-Lactams,' J Am Chem Soc, Mar. 1985 (Mar. 1985), 107(6):1698-701.

Parac-Vogt TN et al., 'Pentacopper(II) Complexes of alpha-Aminohydroxamic Acids: Uranyl-Induced Conversion of a 12-Metallacrown-4 to a 15-Metallacrown-5,' J Inorg Biochem, Nov. 21, 2004 (Nov. 21, 2004) (ePub), 99(2):497-504.

Pittenger C et al., 'The NMDA Receptor as a Therapeutic Target in Major Depressive Disorder,' CNS Neurol Disord Targets, Apr. 2007 (Apr. 2007), 6(2):101-15.

Raghavan B et al., 'Allosteric Modulation of the Dopamine D2 Receptor by Pro-Leu-Gly-NH2 Peptidomimetics Constrained in Either a Polyproline II Helix or a Type II beta-Turn Conformation,' J Med Chem, Apr. 9, 2009 (Apr. 9, 2009), 52(7):2043-51.

Ransom RW and Stec NL, 'Cooperative Modulation of [3H]MK-801 Binding to the N-Methyl-d-Asparate Receptor-Ion Channel Complex by l-Glumate, Glycine, and Polyamines,' J Neurochem, Sep. 1988 (Sep. 1988), 51(3):830-6.

Rasmusson GH et al., '6-Substituted Penicillin Derivatives,' Tetrahedron Lett, 1973 (1973), 14(2):145-8.

Rautio J et al., 'Prodrugs: Design and Clinical Applications,' Nat Rev Drug Discov, Mar. 2008 (Mar. 2008), 7(3):255-70.

Schell MJ, 'The N-methyl D-aspartate Receptor Glycine Site and D-serine Metabolism: An Evolutionary Perspective,' Philos Trans R Soc Lond B Biol Sci, Jun. 29, 2004 (Jun. 29, 2004), 359(1446):943-64.

Shankar GM and Walsh DM, 'Alzheimer's Disease: Synaptic Dysfunction and A-beta,' Mol Neurodegener, Nov. 23, 2009 (Nov. 23, 2009), 4:48-61.

Siemion IZ et al., 'Conformational Preferences of the Sequential Fragments of the Hinge Region of the Human IgA1 Immunoglobulin Molecule,' Biophys Chem, Aug. 1988 (Aug. 1988), 31(1-2):35-44.

Simplicio AL et al a;., 'Prodrugs for Amines,' Molecules, Mar. 2008 (Mar. 2008), 13(3):519-47.

Singapore Search Report and Written Opinion Issued for corresponding Singapore application No. 11201505860X, dated Apr. 18, 2016.

Singapore Search Report and Written Opinion Issued for corresponding Singapore application No. 11201505862T, dated Apr. 18, 2016.

Singapore Search Report and Written Opinion Issued for corresponding Singapore application No. 11201505934X, dated Apr. 27, 2016.

Singapore Search Report and Written Opinion Issued for corresponding Singapore application No. 11201505937S, dated May 5, 2016.

Singapore Search Report and Written Opinion Issued for corresponding Singapore application No. 11201505942Y, dated Mar. 22, 2016.

Stanton PK et al., 'Inhibition of the Production and Maintenance of Long-Term Potentiation in Rat Hippocampal Slices by a Monoclonal Antibody,' Proc Natl Acad Sci USA, Mar. 1987 (Mar. 1987), 84(6):1684-8.

Stanton PK et al., 'Neuroprotection by a Novel NMDAR Functional Glycine Site Partial Agonist, GLYX-13,' Neuroreport, Aug. 26, 2009 (Aug. 26, 2009), 20(13):1193-7.

Tanwar MK et al., 'Gene Expression Microarray Analysis Reveals YLK-40 to be a Potential Serum Marker for Malignant Character in Human Glioma,' Cancer Res, Aug. 1, 2002 (Aug. 1, 2002), 62(15):4364-8.

Thompson LT et al., 'Hippocampus-Dependent Learning Facilitated by a Monoclonal Antibody or D-Cycloserine,' Nature, Oct. 15, 1992 (Oct. 15, 1992), 359(6396):638-41.

Turturro A et al., 'Growth Curves and Survival Characteristics of the Animals Used in the Biomarkers of Aging Program,' J Gerentol A Biol Sci Med Sci, Nov. 1999 (Nov. 1999), 54A(11):B492-B501.

Various, *The NMDA Receptor*, (2nd ed. 1994), GL Collingridge and JC Watkins Eds., Oxford University Press, Inc., New York, New York US (Publ), pp. 1-479 ISBN: 0-19-262371-0.

Wood PL et al., 'Antinociceptive Action of GLYX-13: An N-Methyl-D-aspartate Receptor Glycine Site Partial Agonist,' Neuroreport, Jul. 2, 2008 (Jul. 2, 2008), 19(10)1061-3.

Wood PL, 'The NMDA Receptor Complex: A Long and Winding Road to Therapeutics,' IDrugs, Mar. 2005 (Mar. 2005), 8(3):229-35.

Wood SG et al., 'Tetrapeptide Inhibitors of the IgA1 Proteinases from Type I Neisseria gonorrhoeae,' J Med Chem, Oct. 1989 (Oct. 1989), 32(10):2407-11.

Zhang X-L et al., 'A NMDA Receptor Glycine Site Partial Agonist, GLYX-13, Simultaneously Enhances LTP and Reduces LTD at Schaffer Collateral-CA1 Synapses in Hippocampus,' Neuropharmacology, Aug. 29, 2008 (Aug. 29, 2008), 55(7):1238-50.

SPIRO-LACTAM NMDA RECEPTOR MODULATORS AND USES THEREOF

CROSS REFERENCE TO RELATED APPLICATIONS

This application is a continuation patent application under 35 U.S.C. § 120 of U.S. patent application Ser. No. 14/764,419, filed on Jul. 29, 2015, which application is a U.S. national stage application under 35 U.S.C. § 371 of International Application No. PCT/US2014/013626, filed on Jan. 29, 2014, which claims the benefit of and priority to U.S. Patent Application No. 61/757,939, filed on Jan. 29, 2013, each of which is incorporated by reference herein in its entirety.

BACKGROUND

N-methyl-d-aspartate (NMDA) receptor is a postsynaptic, ionotropic receptor that is responsive to, inter alia, the excitatory amino acids glutamate and glycine and the synthetic compound NMDA. The NMDA receptor controls the flow of both divalent and monovalent ions into the postsynaptic neural cell through a receptor associated channel (Foster et al., Nature 1987, 329:395-396; Mayer et al., Trends in Pharmacol. Sci. 1990, 11:254-260). The NMDA receptor has been implicated during development in specifying neuronal architecture and synaptic connectivity, and may be involved in experience-dependent synaptic modifications. In addition, NMDA receptors are also thought to be involved in long term potentiation and central nervous system disorders.

The NMDA receptor plays a major role synaptic plasticity that underlies many higher cognitive functions, such as memory acquisition, retention and learning, as well as in certain cognitive pathways and in the perception of pain (Collingridge et al., The NMDA Receptor, Oxford University Press, 1994). In addition, certain properties of NMDA receptors suggest that they may be involved in the information-processing in the brain that underlies consciousness itself.

The NMDA receptor has drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptors which opens their ligand-gated ion channels; in turn the calcium influx produces a high level intracellular calcium which activates a biochemical cascade resulting in protein degradation and cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's, and Alzheimer's diseases. Activation of the NMDA receptor has been shown to be responsible for post-stroke convulsions, and, in certain models of epilepsy, activation of the NMDA receptor has been shown to be necessary for the generation of seizures. Neuropsychiatric involvement of the NMDA receptor has also been recognized since blockage of the NMDA receptor $Ca^{++}$ channel by the animal anesthetic PCP (phencyclidine) produces a psychotic state in humans similar to schizophrenia (reviewed in Johnson, K. and Jones, S., 1990). Further, NMDA receptors have also been implicated in certain types of spatial learning.

The NMDA receptor is believed to consist of several protein chains embedded in the postsynaptic membrane. The first two types of subunits discovered so far form a large extracellular region, which probably contains most of the allosteric binding sites, several transmembrane regions looped and folded so as to form a pore or channel, which is permeable to $Ca^{++}$ and a carboxyl terminal region. The opening and closing of the channel is regulated by the binding of various ligands to domains (allosteric sites) of the protein residing on the extracellular surface. The binding of the ligands is thought to affect a conformational change in the overall structure of the protein which is ultimately reflected in the channel opening, partially opening, partially closing, or closing.

NMDA receptor compounds may exert dual (agonist/antagonist) effect on the NMDA receptor through the allosteric sites. These compounds are typically termed "partial agonists". In the presence of the principal site ligand, a partial agonist will displace some of the ligand and thus decrease $Ca^{++}$ flow through the receptor. In the absence of or lowered level of the principal site ligand, the partial agonist acts to increase $Ca^{--}$ flow through the receptor channel.

A need continues to exist in the art for novel and more specific/potent compounds that are capable of binding the glycine binding site of NMDA receptors, and provide pharmaceutical benefits. In addition, a need continues to exist in the medical arts for orally deliverable forms of such compounds.

SUMMARY

Provided herein, at least in part, are compounds that are NMDA modulators, for example, partial agonists of NMDA. For example, disclosed herein are compounds represented by the formula:

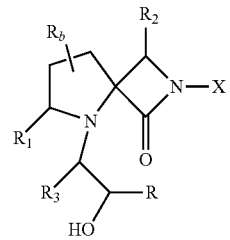

(I)

and pharmaceutically acceptable salts, stereoisomers, and N-oxides thereof, wherein
$R_b$ is selected from the group consisting of H, halogen, hydroxyl, cyano and $C_1$-$C_6$ alkyl;
R is H or $C_1$-$C_6$ alkyl;
$R_1$ is H or $C_1$-$C_6$ alkyl;
$R_2$ is H or $C_1$-$C_6$ alkyl;
$R_3$ is selected from the group consisting of H, $C_1$-$C_6$ alkyl, —OH, $C_1$-$C_6$alkoxy, —$CO_2$H, or —CONR'R', wherein R' for each occurrence is selected from H, $C_1$-$C_6$ alkyl or a nitrogen protecting group; and
X is H or —$C_1$-$C_6$ alkylene-C(O)—X', wherein X' is selected from the group consisting of $C_3$-$C_6$ cycloalkyl, a 4- to 6-membered heterocycloalkyl ring having 1, 2, or 3 heteroatoms selected from O, S, or N, phenyl and 4- to 6-membered heteroaryl ring having 1, 2, or 3 heteroatoms selected from O, S, or N, wherein X' is optionally substituted by one or more substituents selected front the group consisting of halogen, hydroxyl, C$_1$-C$_6$ alkyl and C$_1$-C$_6$ alkoxy; or in other embodiments, the variables set forth in formula (I) can be as defined as follows:

R$_b$ is selected from the group consisting of H, halogen, hydroxyl, cyano and C$_1$-C$_6$ alkyl;
R is H or C$_1$-C$_6$ alkyl;
R$_1$ is H or C$_1$-C$_6$ alkyl;
R$_2$ is H or C$_1$-C$_6$ alkyl;
R$_3$ is selected from the group consisting of H, C$_1$-C$_6$ alkyl, —OH, C$_1$-C$_6$ alkoxy, —CO$_2$H, or —CONR'R', wherein R' for each occurrence is independently selected from H, C$_1$-C$_6$ alkyl or a nitrogen protecting group; and
X is H, X', alkylene-X', or —C$_1$-C$_6$ alkylene-C(O)—X', wherein X' is selected from the group consisting of:
(i) C$_3$-C$_6$ cycloalkyl;
(ii) heterocyclyl including from 3 to 6 ring atoms wherein 1, 2, or 3 of the ring atoms are independently selected from the group consisting of N, NH, N(C1-C3 alkyl), O and S;
(iii) phenyl; and
(iv) heteroaryl including from 5 to 6 ring atoms wherein 1, 2, or 3 of the ring atoms are independently selected from the group consisting of N, NH, N(C1-C3 alkyl), O, and S;
wherein X' is optionally substituted by one, two or three substituents independently selected from the group consisting of halogen, hydroxyl, C$_1$-C$_6$ alkyl and C$_1$-C$_6$ alkoxy.

In another aspect, disclosed compounds include those represented by the formula:

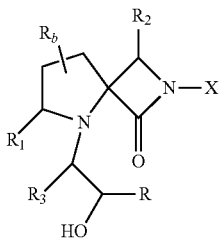

and pharmaceutically acceptable salts, stereoisomers, and N-oxides thereof, wherein
R$_b$ is selected from the group consisting of H, halogen, hydroxyl, cyano and C$_1$-C$_6$ alkyl;
R is H or methyl;
R$_1$ is H or methyl;
R$_2$ is H or methyl;
R$_3$ is selected from the group consisting of H, C$_1$-C$_6$ alkyl, —OH, C$_1$-C$_6$ alkoxy, —CO$_2$H, or —CONR'R', wherein R' for each occurrence is selected from H, C$_1$-C$_6$ alkyl or a nitrogen protecting group; and
X is H or —C$_1$-C$_6$ alkylene-C(O)—NR$^c$R$^d$;
R$^c$ and R$^d$, together with the nitrogen to which they are attached, form a 4-6 membered heterocyclic ring, which may have an additional heteroatom selected from O, S, or N; wherein the 4-6 membered heterocyclic ring may optionally be substituted by one or more substituents selected from the group consisting of halogen, cyano, oxo, and C$_1$-C$_6$alkyl.

Also provided herein are pharmaceutically acceptable compositions comprising a disclosed compound, and a pharmaceutically acceptable excipient. For example, such compositions may be suitable for oral or intravenous administration to a patient.

In another aspect, a method of treating a condition selected from the group consisting of autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder, phobia, post-traumatic stress syndrome, a behavior disorder, an impulse control disorder, a substance abuse disorder, a sleep disorder, a memory disorder, a learning disorder, urinary-incontinence, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, Tourette's syndrome, epilepsy, cerebral ischemia, stroke, a brain tumor, traumatic brain injury, cardiac arrest, myelopathy, spinal cord injury, peripheral neuropathy, acute neuropathic pain, and chronic neuropathic, in a patient in need thereof is provided. Such methods may comprise administering to the patient a pharmaceutically effective amount of a disclosed compound or pharmaceutically acceptable salts, stereoisomers, N-oxides, and hydrates thereof.

In some embodiments, a contemplated method includes treating depression. For example, depression may include one or more of major depressive disorder, dysthymic disorder, psychotic depression, postpartum depression, seasonal affective disorder, bipolar disorder, mood disorder, or depression caused by a chronic medical condition. In other embodiments, a contemplated method may treat schizophrenia. Such schizophrenia may be, for example, paranoid type schizophrenia, disorganized type schizophrenia, catatonic type schizophrenia, undifferentiated type schizophrenia, residual type schizophrenia, post-schizophrenic depression, or simple schizophrenia.

DETAILED DESCRIPTION

This disclosure is generally directed to compounds that are capable of modulating NMDA, NMDA antagonists or partial agonists, and compositions and/or methods of using the disclosed compounds.

Definitions

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having t least one carbon-carbon double bond, such as a straight or branched group of 2-6 or 3-4 carbon atoms, referred to herein for example as C$_2$-C$_6$alkenyl, and C$_3$-C$_4$ alkenyl, respectively. Exemplary alkenyl groups include, but are not limited to, vinyl, allyl, butenyl, pentenyl, etc.

The term "alkoxy" as used herein refers to a straight or branched alkyl group attached to an oxygen (alkyl-O—). Exemplary alkoxy groups include, but are not limited to, alkoxys of 1-6 or 2-6 carbon atoms, referred to herein as C$_1$-C$_6$ alkoxy, and C$_2$-C$_6$ alkoxy, respectively. Exemplary alkoxy groups include, but are not limited to methoxy, ethoxy, isopropoxy, etc.

The term "alkenyloxy" used herein refers to a straight or branched alkenyl group attached to an oxygen (alkenyl-O). Exemplary alkoxy groups include, but are not limited to, groups with an alkenyl group of 3-6 carbon atoms, (also e.g.

referred to as $C_3$-$C_6$alkenyloxy). Exemplary "alkoxy" groups include, but are not limited to allyloxy, butenyloxy, etc.

The term "alkynyloxy" used herein refers to a straight or branched alkynyl group attached to an oxygen (alkynyl-O)). Exemplary alkynyloxy groups include, but are not limited to, $C_3$-$C_6$alkynyloxy, e.g., propynyloxy.

The term "alkyl" as used herein refers to a saturated straight or branched hydrocarbon, such as a straight or branched group of 1-6, 1-4, or 1-3 carbon atoms, referred to herein as $C_1$-$C_6$alkyl, $C_1$-$C_4$alkyl, and $C_1$-$C_3$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc. The term "haloalkyl" as used herein refers to a saturated straight or branched alkyl groups, in which one or more hydrogen atoms of the alkyl group are replaced with one or more independently selected halogens. The term "haloalkyl" encompasses alkyl groups in which all of hydrogen atoms of the alkyl group are replaced independently selected halogens (sometimes referred to as "perhalo" alkyl groups. Exemplary haloalkyl groups include, but are not limited to, $CH_2F$, $CH_2CH_2Cl$, $CF_3$, $CHFCH_2Cl$.

The term "alkynyl" as used herein refers to an unsaturated straight or branched hydrocarbon having at least one carbon-carbon triple bond, such as a straight or branched group of 2-6, or 3-6 carbon atoms, referred to herein as $C_2$-$C_6$alkynyl, and $C_3$-$C_6$alkynyl, respectively. Exemplary alkynyl groups include, but are not limited to, ethynyl, propynyl, butynyl, pentynyl, hexynyl, methylpropynyl, etc.

The term "bridged cycloalkyl" as used herein, is defined as a monocyclic 4- to 7-membered cycloalkyl group in which two non-adjacent atoms are linked by a $CH_2$ or $CH_2CH_2$ group. A "bridged cycloalkyl" may be fused to one or more phenyl, partially unsaturated, or saturated rings. Examples of bridged carbocyclic groups include but are not limited to bicyclo[2.2.1]heptane, bicyclo[2.2.2]octane bicyclo[2.2.2]octene etc.

The term "carbonyl" as used herein refers to the radical —C(O)—. The term "cyano" as used herein refers to the radical —CN. The term "nitro" refers to the radical —$NO_2$. The term "H" refers to hydrogen.

The term "cycloalkoxy" as used herein refers to a cycloalkyl group attached to an oxygen (cycloalkyl-O—).

The term "cycloalkyl" as used herein refers to a monocyclic saturated or partially unsaturated hydrocarbon group of for example 3-6, or 4-6 carbons, referred to herein, e.g., as "$C_{3-6}$ cycloalkyl" or "$C_{4-5}$cycloalkyl," and derived from a cycloalkane. Exemplary cycloalkyl groups include, but are not limited to, cyclohexyl, cyclohexenyl, cyclopentyl, cyclobutyl, cyclopropyl or cyclopentyl.

The terms "halo" or "halogen" as used herein refer to F, Cl, Br, or I.

The terms "heteroaryl" as used herein refers to a monocyclic aromatic 4-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furyl, thienyl, pyrrolyl, thiazolyl, oxazolyl, isothiazolyl, isoxazolyl, imidazolyl, pyrazolyl, triazolyl, oxadiazolyl (e.g., 1,2,4-oxadiazolyl or 1,3,4-oxadiazolyl), pyridyl, and pyrimidinyl.

The term "heterocyclyl" or "heterocyclic group" are art-recognized and refer to saturated or partially unsaturated 4- to 7-membered ring structures, whose ring structures include one to three heteroatoms, such as nitrogen, oxygen, and sulfur. A heterocycle may be fused to one or more phenyl, partially unsaturated, or saturated rings. Examples of heterocyclyl groups include but are not limited to pyrrolidinyl, piperidinyl, morpholino, thiomorpholino, and piperazinyl.

The term "heterocyclylalkoxy" as used herein refers to a heterocyclyl-alkyl-O— group.

The term "heterocyclyloxyalkyl" refers to a heterocyclyl-O-alkyl- group.

The term "heterocycloxy" refers to a heterocyclyl-O— group. The term "cycloalkyloxy" refers to a cycloalkyl-O— group.

The term "heteroaryloxy" referes to a heteroaryl-O— group.

The terms "hydroxy" and "hydroxyl" as used herein refers to the radical —OH.

The term "oxo" as used herein refers to the radical =O.

The term "nitrogen protecting group" or "amino protecting group" is art-recognized and as used herein refers to a chemical moiety that is covalently linked to a nitrogen atom of an amino (primary or secondary) group and that temporarily blocks the reactivity of the amino group during a synthetic step and is selectively removed once the synthetic step is complete. Nitrogen protecting groups include, for example, 9-Fluorenylmethyloxycarbonyl (Fmoc), tert-butoxycarbonyl (Boc), carbobenzyloxycarbonyl (Cbz), p-methoxybenzyloxycarbonyl, acetyl, trifluoroacetyl, benzoyl, phthalimido, benzyl (Bn), p-methoxybenzyl, p-methoxyphenyl, 3,4-dimethoxybenzyl, triphenylmethyl, benzylidene, and p-toluenesulfonyl (Ts). In some embodiments, the nitrogen protecting group can have one of the following formulas: —C(O)O$R_{31}$ or —C(O)$R_{32}$ as defined herein. In certain embodiments, $R_{31}$ is selected from the group consisting of: $C_1$-$C_6$ alkyl; $C_1$-$C_6$ haloalkyl; $C_2$-$C_6$ alkenyl; $C_2$-$C_6$ alkynyl; $C_3$-$C_{10}$ cycloalkyl, wherein the $C_3$-$C_{10}$ cycloalkyl is optionally substituted with from 1-3 independently selected $C_1$-$C_3$ alkyl; —$CH_2$—$C_3$-$C_{10}$ cycloalkyl wherein the $C_3$-$C_{10}$ cycloalkyl is optionally substituted with from 1-3 independently selected $C_1$-$C_3$ alkyl; —$CH_2$-phenyl, wherein the phenyl is optionally substituted with from 1-2 substituents independently selected from $C_1$-$C_3$ alkyl, $C_1$-$C_3$ haloalkyl, $C_1$-$C_3$ alkoxy, $C_1$-$C_3$ haloalkoxy, nitro, halo, $SO_2Me$, cyano, and —OC(O)$CH_3$; and —$CH_2$-pyridyl. In certain embodiments, $R_{32}$ is selected from the group consisting of: H; $C_1$-$C_6$ alkyl; $C_1$-$C_6$ haloalkyl; phenyl, wherein the phenyl is optionally substituted with from 1-2 substituents independently selected from $C_1$-$C_3$ alkyl, $C_1$-$C_3$ haloalkyl, $C_1$-$C_3$ alkoxy, $C_1$-$C_3$ haloalkoxy, nitro, halo, $SO_2Me$, cyano, and —OC(O)$CH_3$; and pyridyl.

As used in the present disclosure, the term "partial NMDA receptor agonist" generally refers to a compound that is capable of binding to a glycine binding site of an NMDA receptor; at low concentrations a NMDA receptor agonist acts substantially as agonist and at high concentrations it acts substantially as an antagonist. These concentrations are experimentally determined for each and every "partial agonist."

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment e.g., of pain or depression is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in lessening a symptom of depression.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diasteremners. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers or diastereomers. The enantiomer and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds of the present invention. The symbol ≡≡≡ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consist of all geometric isomers, enantiomers or diastereomers. The present invention encompasses various stereoisomers of these compounds and mixtures thereof.

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using steroselective chemical or enzymatic reagents. Racemic mixtures can also be resolved into their component enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the ad. Stereoselective syntheses encompass both enantio- and diastereoselective transformations. For examples, see Carreira and Kvaemo, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{13}F$, and $^{36}Cl$, respectively. For example, a compound of the invention may have one or more H atom replaced with deuterium.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g. Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$) alkylcarbamoyl-($C_1$-$C_2$)alkyl and piperidino-, pyrrolidino- or morpholino($C_2$-$C_3$)alkyl.

Similarly, if a compound of the invention contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-acyloxyakyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

Compounds

Disclosed compounds include those represented by the formula:

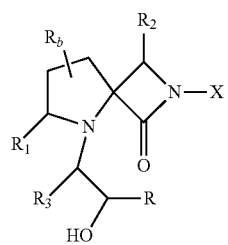

(I)

and pharmaceutically acceptable salts, stereoisomers, and N-oxides thereof, wherein $R_b$ is selected from the group consisting of H, halogen, hydroxyl, cyano and $C_1$-$C_6$ alkyl;

R is H or $C_1$-$C_6$ alkyl;

$R_1$ is H or $C_1$-$C_6$ alkyl;

$R_2$ is H or $C_1$-$C_6$ alkyl;

$R_3$ is selected from the group consisting of H, $C_1$-$C_6$ alkyl, —OH, $C_1$-$C_6$ alkoxy, —$CO_2H$, or —CONR'R', wherein R' for each occurrence is selected from H, $C_1$-$C_6$ alkyl or a nitrogen protecting group; and X is H or —$C_1$-$C_6$ alkylene-C(O)—X', wherein X' is selected from the group consisting of $C_3$-$C_6$ cycloalkyl, a 4- to 6-membered heterocycloalkyl ring having 1, 2, or 3 heteroatoms selected from O, S, or N, phenyl and 4- to 6-membered heteroaryl ring having 1, 2, or 3 heteroatoms selected from O, S, or N, wherein X' is optionally substituted by one or more substituents selected from the group consisting of halogen, hydroxyl, $C_1$-$C_6$alkyl and $C_1$-$C_6$alkoxy; or in other embodiments, the variables set forth in formula (I) can be as defined as follows:

$R_b$ is selected from the group consisting of H, halogen, hydroxyl, cyano and $C_1$-$C_6$ alkyl (e.g., H);

R is H or $C_1$-$C_6$ alkyl;

$R_1$ is H or $C_1$-$C_6$ alkyl;

$R_2$ is H or $C_1$-$C_6$ alkyl;

$R_3$ is selected from the group consisting of H, $C_1$-$C_6$ alkyl, —OH, $C_1$-$C_6$alkoxy, —$CO_2H$, or —CONR'R', wherein R' for each occurrence is independently selected from H, $C_1$-$C_6$ alkyl or a nitrogen protecting group; and X is H, X', —$C_1$-$C_6$ alkylene-X', or —$C_1$-$C_6$ alkylene-C(O)—X', wherein X' is selected from the group consisting of:

(i) $C_3$-$C_6$ cycloalkyl;

(ii) heterocyclyl including from 3 to 6 ring atoms wherein 1, 2, or 3 of the ring atoms are independently selected from the group consisting of N, NH, N(C1-C3 alkyl), O, and S;

(iii) phenyl; and (iv) heteroaryl including from 5 to 6 ring atoms wherein 1, 2, or 3 of the ring atoms are independently selected from the group consisting of N, NH, N(C1-C3 alkyl), O, and S;

wherein X' is optionally substituted by one, two or three substituents independently selected from the group consisting of halogen, hydroxyl, $C_1$-$C_6$ alkyl and $C_1$-$C_6$ alkoxy.

In certain embodiments, R is $C_1$-$C_2$alkyl. In some embodiments, R is methyl. In other embodiments, R is H.

In certain embodiments, $R_1$ is H.

In other embodiments, $R_2$ is H.

In some embodiments, $R_3$ is —CONR'R'. In certain embodiments R' for each occurrence is independently selected from H and a nitrogen protecting group. For example, R' for each occurrence can be H, and $R_3$ is —C(O)$NH_2$. As another example, one R' is H, and the other is a nitrogen protecting group (e.g., as defined anywhere herein, e.g., pare-methoxyphenyl (PMP)).

In some embodiments, X is H or —$C_1$-$C_6$ alkylene-C(O)—X'. In certain embodiments, X is H. In other embodiments, X is —$C_1$-$C_6$ alkylene-C(O)—X' (e.g., —$C_1$-$C_2$ alkylene-C(O)—X' or —$CH_2$—C(O)—X'). In certain embodiments, X' is heterocyclyl including from 3 to 6 (e.g., 5-6 or 5) ring atoms wherein 1, 2, or 3 of the ring atoms are independently selected from the group consisting of N, NH, N(C1-C3 alkyl), O, and S (e.g., N, NH, N(C1-C3 alkyl; e.g., in which the nitrogen atom is attached to C(O)). In certain embodiments, X is

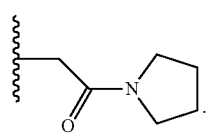 [SMILES: *CC(=O)N1CCCC1]

Embodiments in which X is H or —$C_1$-$C_6$ alkylene-C(O)—X' can include one or more of the following features: R is H or methyl; $R_1$ is H; $R_2$ is H; $R_3$ is —CONR'R' (as defined anywhere herein, e.g., C(O)$NH_2$); $R_b$ is H.

In some embodiments, X is X' or —$C_1$-$C_6$ alkylene-X'. In certain embodiments, X is X'. In other embodiments, X is —$C_1$-$C_6$ alkylene-X' (e.g., —$C_1$-$C_2$ alkylene-X' or $CH_2$—X'). In certain of these embodiments, X' is phenyl that is optionally substituted with halogen, hydroxyl, $C_1$-$C_6$ alkyl or $C_1$-$C_6$ alkoxy (e.g., X' is para-methoxyphenyl (PMP)).

Embodiments in which X is X' or —$C_1$-$C_6$ alkylene-X' can include one or more of the following features: R is H or methyl; $R_1$ is H; $R_2$ is H; $R_3$ is —CONR'R' (as defined anywhere herein, e.g., —C(O)$NH_2$); $R_b$ is H.

In another aspect, disclosed compounds include those represented by the formula:

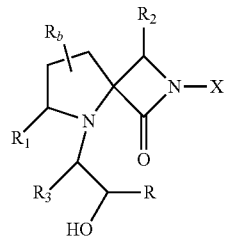

and pharmaceutically acceptable salts, stereoisomers, and N-oxides thereof, wherein $R_b$ is selected from the group consisting of H, halogen, hydroxyl, cyano and $C_1$-$C_6$ alkyl;

R is H or methyl;

$R_1$ is H or methyl;

$R_2$ is H or methyl;

$R_3$ is selected from the group consisting of H, $C_1$-$C_6$ alkyl, —OH, $C_1$-$C_6$ alkoxy, —$CO_2H$, or —CONR'R', wherein R' for each occurrence is selected from H, $C_1$-$C_6$ alkyl or a nitrogen protecting group; and X is H or —$C_1$-$C_6$alkylene-C(O)—$NR_cR^d$;

$R^c$ and $R^d$, together with the nitrogen to which they are attached, form a 4-6 membered heterocyclic which may have an additional heteroatom selected from O, S, or N; wherein the 4-6 membered heterocyclic ring may optionally be substituted by one or more substituents selected from the group consisting of halogen, cyano, oxo, and $C_{1-6}$alkyl.

In some embodiments, a disclosed compound includes any of those delineated in Table 1 and/or the Examples, e.g., one having the formula:

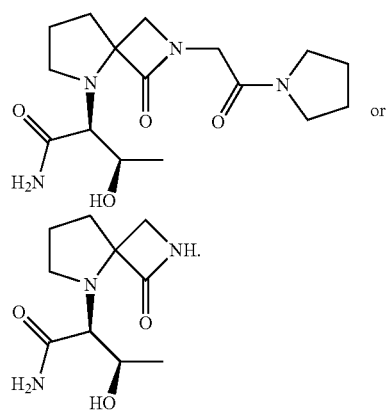

The compounds of the present disclosure and formulations thereof may have a plurality of chiral centers. Each chiral center may be independently R, S, or any mixture of R and S. For example, in some embodiments, a chiral center may have an R:S ratio of between about 100:0 and about 50:50, between about 100:0 and about 75:25, between about 100:0 and about 85:15, between about 100:0 and about 90:10, between about 100:0 and about 95:5, between about 100:0 and about 98:2, between about 100:0 and about 99:1, between about 0:100 and 50:50, between about 0:100 and about 25:75, between about 0:100 and about 15:85, between about 0:100 and about 10:90, between about 0:100 and about 5:95, between about 0:100 and about 2:98, between about 0:100 and about 1:99, between about 75:25 and 25:75, and about 50:50. Formulations of the disclosed compounds comprising a greater ratio of one or more isomers (i.e., R and/or S) may possess enhanced therapeutic characteristic relative to racemic formulations of a disclosed compounds or mixture of compounds.

Disclosed compounds may provide for efficient cation channel opening at the NMDA receptor, e.g. may bind or associate with the glutamate site of the NMDA receptor to assist in opening the cation channel. The disclosed compounds may be used to regulate (turn on or turn off) the NMDA receptor through action as an agonist.

The compounds as described herein may be glycine site NMDA receptor partial agonists. A partial agonist as used in this context will be understood to mean that at a low concentration, the analog acts as an agonist and at a high concentration, the analog acts as an antagonist. Glycine binding is not inhibited by glutamate or by competitive inhibitors of glutamate, and also does not bind at the same site as glutamate on the NMDA receptor. A second and separate binding site for glycine exists at the NMDA receptor. The ligand-gated ion channel of the NMDA receptor is, thus, under the control of at least these two distinct allosteric sites. Disclosed compounds may be capable of binding or associating with the glycine binding site of the NMDA receptor. In some embodiments, disclosed compounds may possess a potency that is 10-fold or greater than the activity of existing NMDA receptor glycine site partial agonists.

The disclosed compounds may exhibit a high therapeutic index. The therapeutic index, as used herein, refers to the ratio of the dose that produces a toxicity in 50% of the population (i.e., $TD_{50}$) to the minimum effective dose for 50% of the population (i.e., $ED_{50}$). Thus, the therapeutic index=$(TD_{50}):(ED_{50})$. In some embodiments, a disclosed compound may have a therapeutic index of at least about 10:1, at least about 50:1, at least about 100:1, at least about 200:1, at least about 500:1, or at least about 1000:1.

Compositions

In other aspects, formulations and compositions comprising the disclosed compounds and optionally a pharmaceutically acceptable excipient are provided. In some embodiments, a contemplated formulation comprises a racemic mixture of one or more of the disclosed compounds.

Contemplated formulations may be prepared in any of a variety of forms for use. By way of example, and not limitation, the compounds may be prepared in a formulation suitable for oral administration, subcutaneous injection, or other methods for administering an active agent to an animal known in the pharmaceutical arts.

Amounts of a disclosed compound as described herein in a formulation may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

The specification for the dosage unit forms of the invention are dictated by and directly dependent on (a) the unique characteristics of the compound selected and the particular therapeutic effect to be achieved, and (b) the limitations inherent in the art of compounding such an active compound for the treatment of sensitivity in individuals.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

The compounds can be administered in a time release formulation, for example in a composition which includes a slow release polymer. The compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In accordance with an alternative aspect of the invention, a compound may be formulated with one or more additional compounds that enhance the solubility of the compound.

Methods

Methods for treating a condition in a patient in need thereof by administering a therapeutically effective dose of a compound described herein are provided. In some embodiments, the condition may be a mental condition. For example, a mental illness may be treated. In another aspect, a nervous system condition may be treated. For example, a condition that affects the central nervous system, the peripheral nervous system, and/or the eye may be treated. In some embodiments, neurodegenerative diseases may be treated.

In some embodiments, the methods include administering a compound to treat patients suffering from autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder (OCD), phobia, post-traumatic stress syndrome, a behavior disorder, an impulse control disorder, a substance abuse disorder (e.g., a withdrawal symptom, opiate addiction, nicotine addiction, and ethanol addition), a sleep disorder, a memory disorder (e.g., a deficit, loss, or reduced ability to make new memories), a learning disorder, urinary incontinence, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, Tourette's syndrome, epilepsy, cerebral ischemia, stroke, a brain tumor, traumatic brain injury, cardiac arrest, myelopathy, spinal cord injury, peripheral neuropathy, acute neuropathic pain, and chronic neuropathic pain.

In some embodiments, methods of treating a memory disorder associated with aging, schizophrenia, special learning disorders, seizures, post-stroke convulsions, brain ischemia, hypoglycemia, cardiac arrest, epilepsy, migraine, AIDS dementia, Huntington's chorea, Parkinson's disease, early stage Alzheimer's disease, and Alzheimer's disease are contemplated.

In certain embodiments, methods for treating schizophrenia are provided. For example, paranoid type schizophrenia, disorganized type schizophrenia (i.e., hebephrenic schizophrenia), catatonic type schizophrenia, undifferentiated type schizophrenia, residual type schizophrenia, post-schizophrenic depression, and simple schizophrenia may be treated using the methods and compositions contemplated herein. Psychotic disorders such as schizoaffective disorders, delusional disorders, brief psychotic disorders, shared psychotic disorders, and psychotic disorders with delusions or hallucinations may also be treated using the compositions contemplated herein.

Paranoid schizophrenia may be characterized where delusions or auditory hallucinations are present, but thought disorder, disorganized behavior, or affective flattening are not. Delusions may be persecutory and/or grandiose, but in addition to these, other themes such as jealousy, religiosity, or somatization may also be present. Disorganized type schizophrenia may be characterized where thought disorder and flat affect are present together. Catatonic type schizophrenia may be characterized where the patient may be almost immobile or exhibit agitated, purposeless movement. Symptoms can include catatonic stupor and waxy flexibility. Undifferentiated type schizophrenia may be characterized where psychotic symptoms are present but the criteria for paranoid, disorganized, or catatonic types have not been met. Residual type schizophrenia may be characterized where positive symptoms are present at a low intensity only. Post-schizophrenic depression may be characterized where a depressive episode arises in the aftermath of a schizophrenic illness where some low-level schizophrenic symptoms may still be present. Simple schizophrenia may be characterized by insidious and progressive development of prominent negative symptoms with no history of psychotic episodes.

In some embodiments, methods are provided for treating psychotic symptoms that may be present in other mental disorders, including, but not limited to, bipolar disorder, borderline personality disorder, drug intoxication, and drug-induced psychosis. In another embodiment, methods for treating delusions (e.g., "non-bizarre") that may be present in, for example, delusional disorder are provided.

Also provided are methods for treating social withdrawal in conditions including, but not limited to, social anxiety disorder, avoidant personality disorder, and schizotypal personality disorder.

In some embodiments, methods are provided for treating neuropathic pain. The neuropathic pain may be acute or chronic. In some cases, the neuropathic pain may be associated with a condition such as herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, and cancer chemotherapeutic-induced neuropathic pain. Methods for enhancing pain relief and for providing analgesia to a patient are also contemplated.

Further contemplated methods include a method of treating autism and/or an autism spectrum disorder in a patient need thereof, comprising administering an effective amount of a compound to the patient. In an embodiment, a method for reducing the symptoms of autism in a patient in need thereof is contemplated, comprising administering an effective amount of a disclosed compound to the patient. For example, upon administration, the compound may decrease the incidence of one or more symptoms of autism such as eye contact avoidance, failure to socialize, attention deficit, poor mood, hyperactivity, abnormal sound sensitivity, inappropriate speech, disrupted sleep, and perseveration. Such decreased incidence may be measured relative to the incidence in the untreated individual or an untreated individual(s).

Also provided herein is a method of modulating an autism target gene expression in a cell comprising contacting a cell with an effective amount of a compound described herein. The autism gene expression may be for example, selected from ABAT, APOE, CHRNA4, GABRA5, GFAP, GRIN2A, PDYN, and PENK. In another embodiment, a method of modulating synaptic plasticity in a patient suffering from a synaptic plasticity related disorder is provided, comprising administering to the patient an effective amount of a compound.

In another embodiment, a method of treating Alzheimer's disease, or e.g., treatment of memory loss that e.g., accompanies early stage Alzheimer's disease, in a patient in need thereof is provided, comprising administering a compound. Also provided herein is a method of modulating an Alzheimer's amyloid protein (e.g., beta amyloid peptide, e.g. the isoform $A\beta_{1-42}$), in-vitro or in-vivo (e.g. in a cell) comprising contacting the protein with an effective amount of a compound is disclosed. For example, in some embodiments, a compound may block the ability of such amyloid protein to inhibit long-term potentiation in hippocampal slices as well as apoptotic neuronal cell death. In some embodiments, a disclosed compound may provide neuroprotective properties to a Alzheimer's patient in need thereof, for example, may provide a therapeutic effect on later stage Alzheimer's-associated neuronal cell death.

In a further embodiment, a method of treating depression comprising administering a compound described herein is provided. In some embodiments, the treatment may relieve depression or a symptom of depression without affecting behavior or motor coordination and without inducing or promoting seizure activity. Exemplary depression conditions that are expected to be treated according to this aspect of the invention include, but are not limited to, major depressive disorder, dysthymic disorder, psychotic depression, postpartum depression, premenstrual syndrome, premenstrual dysphoric disorder, seasonal affective disorder (SAD), bipolar disorder (or manic depressive disorder), mood disorder, and depressions caused by chronic medical conditions such as cancer or chronic pain, chemotherapy, chronic stress, and post traumatic stress disorders. In addition, patients suffering from any form of depression often experience anxiety. Various symptoms associated with anxiety include fear, panic, heart palpitations, shortness of breath, fatigue, nausea, and headaches among others. Anxiety or any of the symptoms thereof may be treated by administering a compound as described herein.

Also provided herein are methods of treating a condition in treatment-resistant patients, e.g., patients suffering front a mental or central nervous system condition that does not, and/or has not, responded to adequate courses of at least one, or at least two, other compounds or therapeutics. For example, provided herein is a method of treating depression in a treatment resistant patient, comprising a) optionally identifying the patient as treatment resistant and b) administering an effective dose of a compound to said patient.

In some embodiments, a compound described herein may be used for acute care of a patient. For example, a compound may be administered to a patient to treat a particular episode (e.g., a severe episode) of a condition contemplated herein.

Also contemplated herein are combination therapies comprising a compound in combination with one or more other active agents. For example, a compound may be combined with one or more antidepressants, such as tricyclic antidepressants, MAO-I's, SSRI's, and double and triple uptake inhibitors and/or anxiolytic drugs. Exemplary drugs that may be used in combination with a compound include Anafranil, Adapin, Aventyl, Elavil, Norpramin, Painelor, Pertofrane, Sinequan, Surmontil, Tofranil, Vivactil, Parnate, Nardil, Marplan, Celexa, Lexapro, Luvox, Paxil, Prozac, Zoloft, Wellbutrin, Effexor, Remeron, Cymbalta, Desyrel (trazodone), and Ludiomill. In another example, a compound may be combined with an antipsychotic medication. Non-limiting examples of antipsychotics include butyrophenones, phenothiazines, thioxanthenes, clozapine, olanzapine, risperidone, quetiapine, ziprasidone, amisulpride, asenapine, paliperidone, iloperidone, zotepine, sertindole, lurasidone, and aripiprazole. It should be understood that combinations of a compound and one or more of the above therapeutics may be used for treatment of any suitable condition and are not limited to use as antidepressants or antipsychotics.

EXAMPLES

The following examples are provided for illustrative purposes only, and are not intended to limit the scope of the disclosure.

Table 1 below shows some exemplary compounds of the disclosure and provides physiochemical characteristics of the compounds.

TABLE 1

| Compound | Structure | Molecular Weight (Da) | cLogP | tPSA |
| --- | --- | --- | --- | --- |
| Compound X | 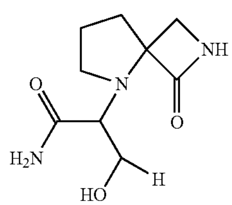 | 213 | −2.20 | 95.7 |
| Compound Y | 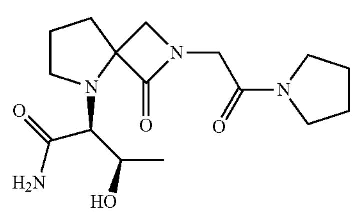 [SMILES: C[C@@H](O)[C@@H](C(N)=O)N1CCCC12CN(CC(=O)N1CCCC1)C2=O] | 338 | −2.04 | 107.2 |
| S5-C5 | 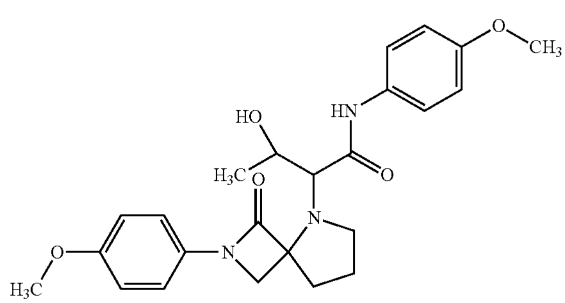 | 439.5042 | 2.02408 | 91.34 |

TABLE 1-continued
| Compound | Structure | Molecular Weight (Da) | cLogP | tPSA |
|---|---|---|---|---|
| S5-C12 | 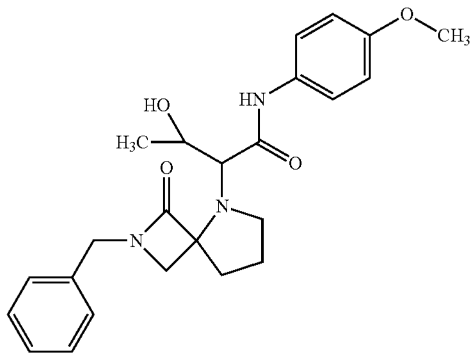 [SMILES: COc1ccc(NC(=O)C(C(C)O)N2CCCC23CN(Cc2ccccc2)C3=O)cc1] | 423.5048 | 2.24827 | 82.11 |
| S5-C11 | 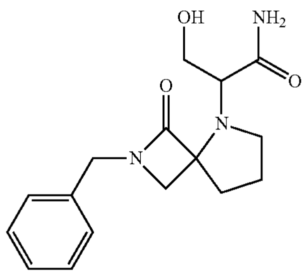 [SMILES: NC(=O)C(CO)N1CCCC12CN(Cc1ccccc1)C2=O] | 303.3562 | −0.251883 | 86.87 |
| S5-C4 | 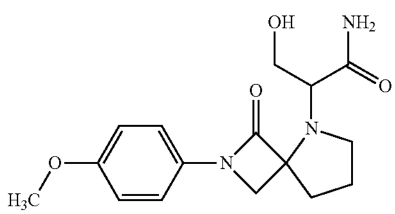 [SMILES: COc1ccc(N2CC3(CCCN3C(CO)C(N)=O)C2=O)cc1] | | | |
| S5-C7 | 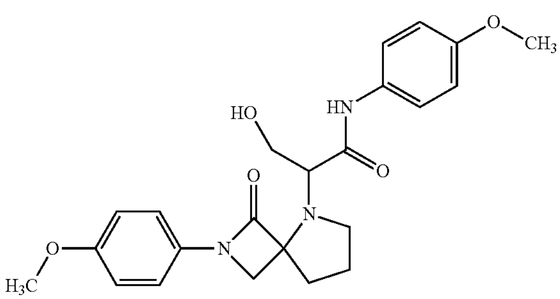 | 425.4776 | 1.6075 | 91.34 |
Example 1—Synthesis of Compound Y
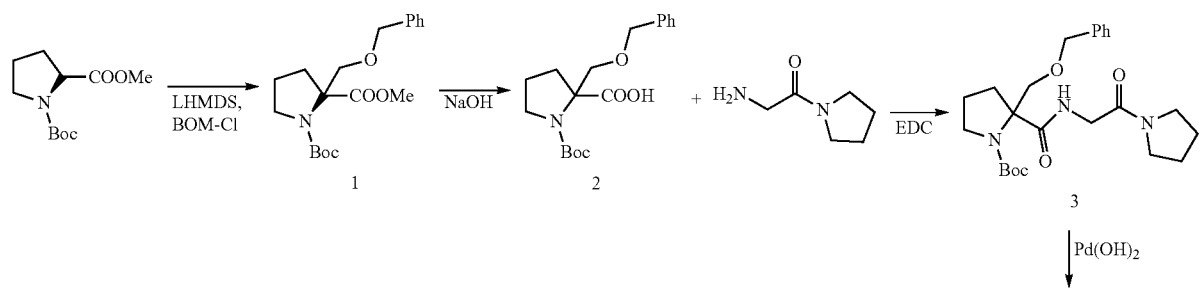
Scheme 1.

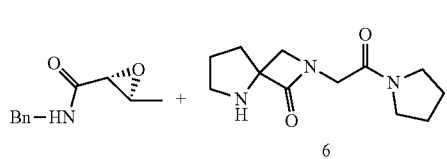 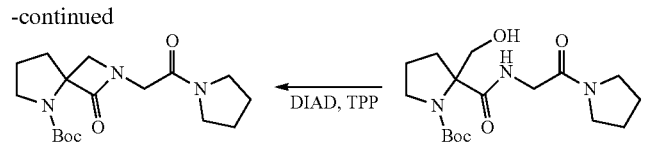

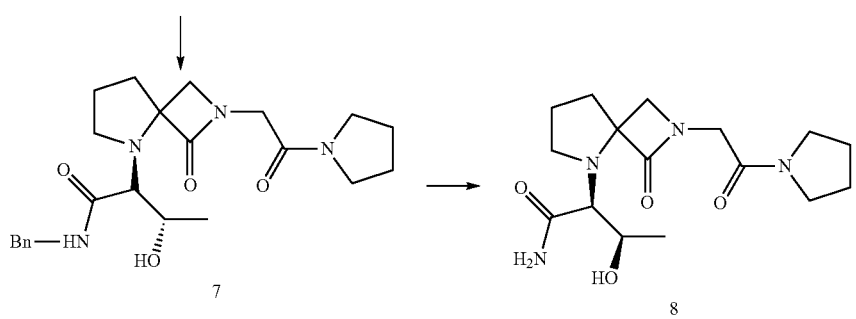

Synthesis of 1-tert-butyl 2-methyl 2-(benzyloxymethyl)pyrrolidine-1,2-dicarboxylate (1)

In a 500 mL 2-neck RBF Boc-Pro-OMe (5 g, 21.83 moles) was dissolved in THF (50 mL) and charged with nitrogen. The resulting reaction mixture was cooled to −45° C. LiHMDS (26 mL, 26.20 mmol) was added drop wise to the reaction mixture at −45° C. The resulting reaction mixture was stirred at −45° C. for 1 h. Benzyl chloromethyl ether (3.14 mL, 26.20 moles) was added drop wise to the reaction mass at −45° C. The resulting reaction mixture was stirred for 1 hr at −45° C. and allowed to rt. After the completion of the reaction, reaction mixture was cooled to 0° C. and quenched with saturated $NH_4Cl$ (20 mL) and extracted with EtOAc (2×25 mL). The combined organic extracts were washed with saturated brine solution. (2×25 mL) and dried over anhydrous $Na_2SO_4$. The organic layer was concentrated under reduced pressure. The obtained crude (6.8 g) material 1 was used for next step without further purification.

Synthesis of 2-(benzyloxymethyl)-1-(tert-butoxycarbonyl)pyrrolidine-2-carboxylic acid (2)

In a 200 mL round bottom flask, 1 (7 g, 20.05 mmol) was taken in a MeOH (50 mL). At 0° C. added 1 M, 5 eq of NaOH solution and stirred, allowed to reach the room temperature and refluxed for 3 hr. After completion of the reaction, the volatiles were evaporated and added water (50 mL). The aqueous layer was acidified using 5% citric acid solution and extracted with ethyl acetate (3×25 mL). The combined organic layer was washed with brine and dried over $Na_2SO_4$. The organic layer was evaporated under reduced pressure to give the analytically pure 2-(benzyloxymethyl)-1-(tert-butoxycarbonyl)pyrrolidine-2-carboxylic acid (2) (4.5 g, 67% yield).

Synthesis of tert-butyl 2-(benzyloxymethyl)-2-(2-oxo-2-(pyrrolidin-1-yl)ethylcarbamoyl)pyrrolidine-1-carboxylate (3)

In a 2-neck 25 mL RBF with guard tube, 2 (3.5 g, 10.44 mmol) was dissolved in THF (30 mL). The reaction kept in ice-salt bath and added NMM (3.5 mL, 31.34 mmol), ECF (1.2 mL, 12.53 mmol). After 10 min of stirring, a solution of 2-amino-1-(pyrrolidin-1-yl)ethanone (3.03 g, 12.53 mmoles) in THF (20 mL) was added. The resulting reaction mixture was stirred at rt for 16 h. After the completion of the reaction, the reaction mixture was concentrated under reduced pressure and diluted with cold water (20 mL) and extracted with EtOAc (2×30 mL). The combined organic extracts were washed with 5% citric acid solution (2×30 mL), saturated $NaHCO_3$ solution (20 mL), brine solution (15 mL) and dried over anhydrous $Na_2SO_4$. The organic layer was concentrated under reduced pressure, purified by column chromatography using 30% ethyl acetate and hexanes to give 3 (2.3 g, yield 49.5%) as colorless oil.

Synthesis of tert-butyl 2-(hydroxymethyl)-2-(2-oxo-2-(pyrrolidin-1-yl)ethylcarbamoyl)pyrrolidine-1-carboxylate (4)

In a steel hydrogenation vessel, 10% Pd—C (200 mg), methanol (20 mL) and 3 (1.7 g, 3.82 mmole) was charged under $N_2$ atmosphere. Reaction mixture was hydrogenated (60 Psi $H_2$ pressure) using Parr hydrogenation at rt for 12 h. The progress of the reaction was monitored by TLC. After completion of the reaction, the reaction mixture was filtered through celite bed and washed with methanol (20 mL). The filtrate was concentrated under reduced pressure to give 4 (1.3 g, yield 96%) which was used without purification for next step.

Synthesis of tert-butyl 1-oxo-2-(2-oxo-2-(pyrrolidin-1-yl)ethyl)-2,5-diazaspiro[3.4]octane-5-carboxylate (5)

To a solution of 4 (1.47 g, 4.15 mmol) in THF (10 mL) at 0° C. temp was added TPP (2.17 g, 8.30 mmol) and DIAD (1.64 mL, 8.30 mmol). To the resulting reaction mixture was stirred at room temperature for 10 min and then sonicated for 3 hr. After completion of the reaction (disappearance of 4 monitored by TLC), volatiles were evaporated under reduced pressure. Column chromatography on silica gel eluted with 50% EtOAc in hexanes afforded 5 (900 mg, yield 64.7%) as gummy oil.

Synthesis of 2-(2-oxo-2-(pyrrolidin-1-yl)ethyl)-2,5-diazaspiro[3.4]octan-1-one (6)

In a 50 mL RBF 5 (2 g, 5.95 mmol) was taken in a DCM (22 mL). At 0° C.; added TFA (6 mL) and stirred at ambient temperature for 1 hr, the reaction was monitored by TLC. After completion of the reaction, the volatiles were evaporated under reduced pressure, neutralized with NH$_4$OH and purified by column chromatography on silica gel eluted with 5% methanol in DCM gave 6 (1.4 g, yield 98%) as gummy solid.

Synthesis of (2R,3S)-3-hydroxy-N-(4-methoxyphenyl)-2-(1-oxo-2-(2-oxo-2-(pyrrolidin-1-yl)ethyl)-2,5-diazaspiro[3.4]octan-5-yl)butanamide (7)

In a 25 mL RBF 6 (50 mg, 0.21 mmol) was taken in a EtOH (7 mL), (2R,3S)—N-(4-methoxyphenyl)-3-methyloxirane-2-carboxamide (48 mg, 0.232 mmol) and added TEA (0.05 mL, 0.27 mmol). The resulting reaction mixture was irradiated to microwaves (1 min×10 times). After completion of the reaction, the volatiles were evaporated under reduced pressure and purified by prep. HPLC to afford 7 (10 mg, yield 5%) gummy oil. $^1$H-NMR: (400 MHz, CDCl$_3$): δ9.34 (s, 1H); 7.46 (d, 2H); 6.83 (d, 2H); 4.25 (d, 1H); 4.17 (d, 1H); 3.66 (d, 3H); 3.47-3.39 (m, 4H); 3.35-3.33 (m, 2H); 3.13-3.09 (m, 2H); 2.33 (q, 2H); 2.16 (q, 1H); 1.96 (q, 3H); 1.85 (q, 3H); 1.25 (d, 3H). HPLC: 99.66% (RT-10.93 min).

Synthesis of (2S,3R)-3-hydroxy-2-(1-oxo-2-(2-oxo-2-(pyrrolidin-1-yl)ethyl)-2,5-diazaspiro[3.4]octan-5-yl)butanamide (Compound Y)

Iodobenzene diacetate (31.2 mg, 0.10 mmol) was dissolved in methanol (3 mL). 7 (12 mg, 0.02 mmol) was dissolved in methanol (2 mL), taken up in a syringe and added to the oxidant solution over 30 min. The syringe was rinsed with methanol (2×1 mL) and the rinses were added to the reaction. The reaction was allowed to stir for an additional 30 min and then acidified with 1 N HCl (1 mL) and allowed to stir for 1.5 h. The reaction mixture was washed with DCM (2×10 mL) and combined organics were back extracted with 0.1 M HCl (1×10 mL), saturated NaHCO$_3$ solution (10 mL), brine solution (5 mL) and dried over anhydrous Na$_2$SO$_4$. The organic layer was concentrated under reduced pressure, purified by column chromatography using 2% MeOH in DCM to give Compound Y (7 mg, 79 yield %) as colorless oil. $^1$H-NMR: (400 MHz, CDCl$_3$): δ7.22 (d, 1H); 6.86 (d, 1H); 6.21 (d, 1H); 6.18 (d, 1H); 5.48 (s, 1H); 5.03-5.08 (m, 1H); 4.37-4.21 (m, 2H); 4.10 (d, 2H); 3.90 (d, 1H); 3.71 (d, 2H); 2.59-2.54 (m, 2H); 2.26-2.12 (m, 2H); 1.97 (q, 3H); 1.90 (q, 3H); 1.50 (d, 3H).

Preparation of Key Intermediates

Scheme I-1, preparation of intermediate I-5

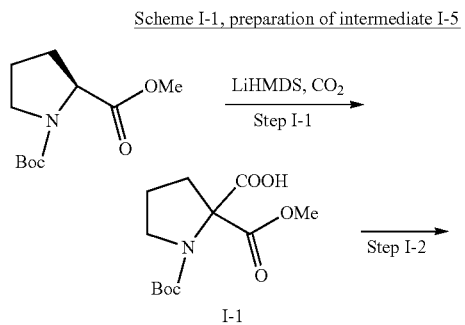

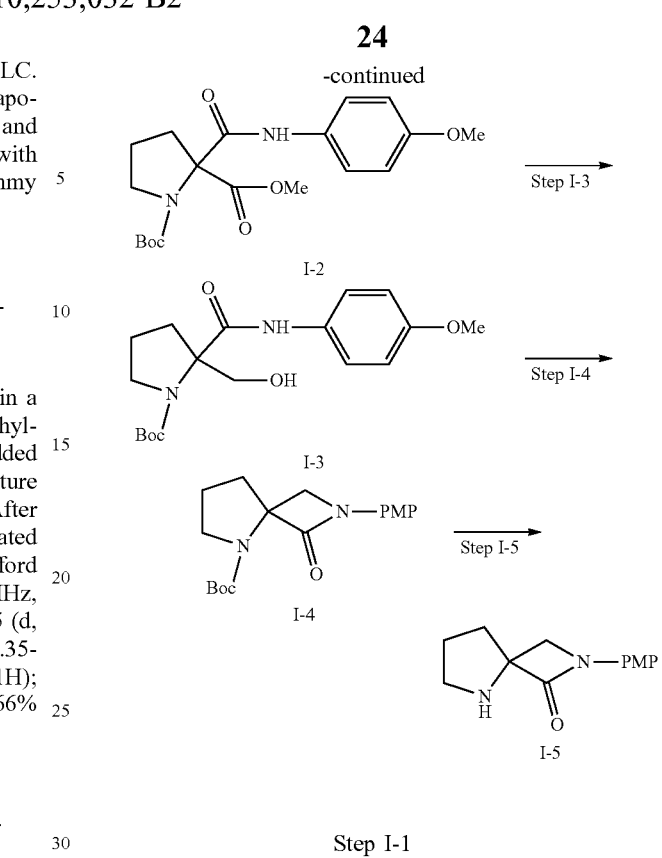

Step I-1

Syntheses of 1-(tert-butoxycarbonyl) 4-(methoxycarbonyl) pyrrolidine-2-carboxylic acid To a stirred solution of Boc-Pro-OMe (20 g, 87.33 mmoles) in dry tetrahydrofuran (200 mL) was added LiHMDS (113 mL, 113.5 mmoles) at −45° C. and stirred for 1 h. Carbon dioxide gas bubbled into the reaction for 1 h at −45° C. After completion of the starting material, reaction mixture was poured into cold water. The aqueous layer was acidified with 1N HCl at 0° C. and extracted with ethyl acetate (3×50 mL). The combined organic layers were washed with brine solution and dried over anhydrous Na$_2$SO$_4$ and concentrated under vacuum to give I-1 (12.4 g, yield: 49.0%) as a gummy liquid.

TLC system: 50% EtOAe-Hexane
Rf-value: 0.2
Visualization: Ninhydrine stain
Analytical Data:
Mass (m/z): 174.1 (M-Boc)$^+$ Step I-2

Synthesis of 1-tert-butyl 2-methyl 2-(4-methoxyphenyl carbamoyl) pyrrolidine-1,2-dicarboxylate To a solution of I-1 (15.4 g, 55.59 mmoles) in dichloromethane (160 mL) was added 4-methoxy aniline (6.83 g, 55.59 mmoles) in presence of NMM (12.47 mL, 111.18 mmoles). EDC.HCl (12.93 g, 83.39 mmoles) was added to the reaction mixture at 0° C. and allowed to stir at rt for 12 h. After the completion of reaction, the reaction mixture was diluted with DCM (100 mL). The organic layer was washed with cold water, 10% aq. citric acid, 5% aq. sodium bicarbonate, brine solution and dried over anhydrous Na$_2$SO$_4$ and concentrated under vacuum to give 1-tert-butyl 2-methyl 2-(4-methoxyphenyl carbamoyl) pyrrolidine-1, 2-dicarboxylate, I-2, (12.6 g, yield: 60.2%) as gummy liquid.
TLC system: 50% EtOAe-Hexane
Rf-value: 0.2
Visualization: UV & Ninhydrin stain
Analytical Data:
Mass (m/z): 279.2 (M-Boc)+

Step I-3

Synthesis of tert-butyl 2-(hydroxymethyl)-2-(4-methoxypheneylcarbamoyl) pyrrolidine-1-carboxylate To a solution of I-2 (12 g, 31.74 mmoles) in MeOH (120 mL) was added Lithium bromide (16.56 g, 190.46 mmoles) and sodium borohydride (7.22 g, 190.46 mmoles), the reaction mixture was allowed to stir for 12 h. After the completion of reaction, methanol was evaporated under reduced pressure. The reaction mixture was quenched with water and extracted with ethyl acetate (3×100 mL). The combined organic layers were washed with brine solution and dried over anhydrous $Na_2SO_4$ and concentrated under vacuum to get crude. The crude was purified by column chromatography (100-200 mesh silica gel, 50% EtOAc in hexane) to give I-3 (5.5 g, yield 49.7%) as white solid.
TLC system: 50% EtOAc-Hexane
Rf-value: 0.3
Visualization: UV & Ninhydrin stain
Mass (m/z): 251.1 (M-Boc)+

Step I-4

Synthesis of tert-butyl 2-(4-methoxyphenyl)-1-oxo-2, 5-diazaspiro [3,4] octane-5-carboxylate To a solution of I-3 (5.5 g, 15.76 mmoles) in dry tetrahydrofuran (20 were added triphenylphosphine (8.26 g, 31.51 mmoles) and DIAD (6.36 mL, 31.51 mmoles). The mixture was sonicated for 3 h. After the completion of reaction, the solvent was evaporated under reduced pressure, the crude material was purified by column chromatography (100-200 mesh silica gel, 40% EtOAc in hexane) to give of I-4 (3.64 g, yield: 70%) as gummy syrup.
TLC system: 50% EtOAc-Hexane
Rf-value: 0.3
Visualization: UV & Ninhydrin stain
Analytical Data:
Mass (m/z): 333.1 (M+H)+

Step I-5

Synthesis of 2-(4-methoxyphenyl)-2, 5-diazaspiro [3,4] octan-1-one

To a solution of I-4 (3.64 g, 10.99 moles) in dichloromethane (30 mL) was added trifluoroacetic acid (15 mL) at 0° C. The reaction mixture was warmed to room temperature and stirred for 2 h. After the completion of reaction, the solvent was evaporated under reduced pressure to get crude compound. The crude compound was dissolved in methanol (5 mL) and basified with aqueous ammonia solution at 0° C. The crude compound was purified by column chromatography (100-200 mesh silica gel, 5% Methanol in DCM) to give I-5 (2.04 g, yield: 80%) as a pale yellow solid.
TLC system: 100% EtOAc
Rf-value: 0.1
Visualization: UV & Ninhydrin stain
Analytical Data:
$^1$H NMR (400 MHz, CDCl$_3$): δ7.26 (d, 2H), 6.86 (d, 2H), 3.70 (s, 3H), 3.64 (d, 1H), 3.59 (d, 1H), 3.22 (m, 1H), 3.05 (m, 1H), 2.26 (m, 1H), 2.08-2.02 (m, 2H), 1.84 (m, 2H).

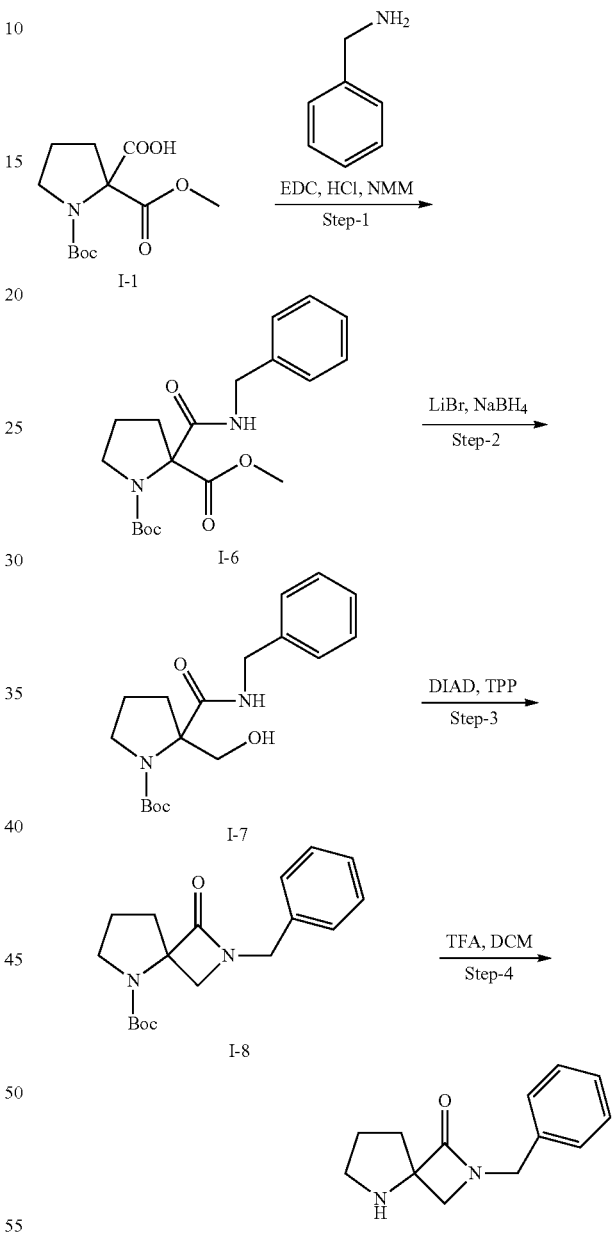

Scheme I-2

Step-1

Synthesis of 1-tert-butyl 2-methyl 2-(benzylcarbamoyl) pyrrolidine-1, 2-dicarboxylate Referring to Scheme I-2, to a stirred solution of I-1 (6.0 g, 21.58 mmoles) in dichloromethane (100 mL) at rt under nitrogen atmosphere. The reaction was cooled to −5° C. added N-methyl morpholine (4.79 mL, 43.16 mmoles) and EDC.HCl (5.02 g, 32.37 mmoles). Benzyl amine (2.2 g, 21.58 mmoles) was added to the reaction mixture and stirred for 12 h at rt. After the completion of reaction, the reaction mixture was concentrated under reduced pressure to get a residue. The residue was dissolved in ethyl acetate (100 mL) and washed with 10% citric acid, 5% sodium bicarbonate, brine solution and dried over anhydrous $Na_2SO_4$ and concentrated under vacuum to get crude. The obtained crude was purified by column chromatography (100-200 mesh silica gel, 25% EtOAc in hexane) to give 1-tert-butyl 2-methyl 2-(benzylcarbamoyl) pyrrolidine-1, 2-dicarboxylate, I-6, (4.0 g, yield: 55.5%) as light yellow liquid.

TLC system: 50% EtOAc-Hexane
Rf-value: 0.4
Visualization: UV & Ninhydrin stain
Analytical Data
$^1$H NMR (400 MHz, $CDCl_3$): $\delta$8.43 (br, 1H), 7.31-7.28 (m, 5H), 4.53-4.46 (m, 2H), 3.75 (s, 3H), 3.72 (t, 1H), 3.53 (d, 1H), 2.94 (t, 1H), 2.20 (d, 1H), 2.03-1.92 (m, 2H), 1.63 (s, 9H).
Mass (m/z): 263.2 (M-Boc)$^+$ Step-2

Synthesis of tert-butyl 2-(benzylcarbamoyl)-2-(hydroxymethyl) pyrrolidine-1-carboxylate To a solution of I-6 (4.0 g, 11.04 mmoles) in methanol (50 mL) was added lithium bromide (9.61 g, 110.4 mmoles), sodium borohydride (4.2 g, 110.4 mmoles) and stirred at rt for 12 h. After the completion of reaction, methanol was evaporated under reduced pressure to get crude. The crude was quenched with water and extracted with ethyl acetate (2×50 mL). The combined organic layers were washed with brine solution and dried over anhydrous $Na_2SO_4$ and concentrated under vacuum to get crude. The crude was purified by column chromatography (100-200 mesh silica gel, 30% EtOAc-Hexane) to give tert-butyl 2-(benzylcarbamoyl)-2-(hydroxymethyl) pyrrolidine-1-carboxylate, I-7, (2.3 g, yield: 62.3%) as white solid.

TLC system: 50% EtOAc-Hexane
Rf-value: 0.3
Visualization: UV & phosphomolybdic acid stain
Analytical Data:
$^1$H NMR (400 MHz, $CDCl_3$): $\delta$7.35-7.28 (m, 5H), 6.90 (br, s, 1H), 4.46 (m, 2H), 4.03 (s, 1H), 3.88 (s, 1H), 3.62-3.56 (m, 2H), 3.49 (d, 2H), 3.42 (s, 1H), 2.61 (d, 1H), 2.31 (m, 1H), 1.59 (s, 9H).
Mass (m/z): 235.2 (M-Boc)$^+$ Step-3

Synthesis of tert-butyl 2-benzyl-1-oxo-2, 5-diazaspiro [3, 4] octane-5-carboxylate To a solution of I-7 (2.30 g, 6.88 mmoles) and triphenyl phosphine (3.61 g, 13.77 mmoles) in dry tetrahydrofuran (30 mL) were stirred at rt under nitrogen atmosphere. Diisopropyl azodicarboxylate (2.78 mL, 13.77 mmoles) was added to the reaction mixture at rt. The resulting reaction mixture was sonicated for 4 h. After the completion of reaction, the reaction was concentrated under reduced pressure to get crude. The crude material was purified by column chromatography (100-200 mesh silica gel, 30% EtOAc in hexane) to give tert-butyl 2-benzyl-1-oxo-2, 5-diazaspiro [3, 4] octane-5-carboxylate, I-8, (1.74 g, yield 80%) as a pale yellow liquid.

TLC system: 50% EtOAc-Hexane
Rf-value: 0.4
Visualization: UV & phosphomolybdic acid stain
Analytical Data:
$^1$H NMR (400 MHz, $CDCl_3$): $\delta$7.37-7.28 (m, 5H), 4.88 (d, 1H), 3.89 (d, 1H), 3.51-3.49 (m, 2H), 3.08 (d, 114), 2.40-2.35 (m, 1H), 2.09 (d, 2H), 1.9-1.91 (m, 1H), 1.78-1.74 (m, 1H), 1.46 (s, 9H).
Mass (m/z): 216.2 (M-Boc)$^+$ Step-4

Synthesis of 2-benzyl-2, 5-diazaspiro [3,4] octan-1-one

To a solution of I-8 (700 mg, 2.21 mmoles) in dichloromethane (10 mL) was added trifluoroacetic acid (5 mL) at room temperature and stirred for 2 h. After the completion of reaction, the reaction mixture was concentrated under reduced pressure and quenched with ice water. The aqueous layer was basified with ammonia solution up to $P^H$~10 and concentrated under reduced pressure to get crude compound. The crude compound was purified by column chromatography (100-200 mesh silica gel, 5% Methanol in DCM) to give 2-benzyl-2, 5-diazaspiro [3, 4] octan-1-one, I-9, (400 mg, yield: 83.7%) as a pale green syrup.

TLC system: 10% Methanol-DCM
Rf-value: 0.3
Visualization: UV & phosphomolybdic acid stain
Analytical Data:
$^1$H NMR (400 MHz, $CDCl_3$): $\delta$7.36-7.22 (m, 5H), 4.38 (q, 2H), 3.20-3.13 (m, 3H), 3.01-2.97 (m, 1H), 2.21-2.18 (m, 1H), 2.02-1.99 (m, 1H), 1.99-1.91 (m, 1H), 1.85-1.80 (m, 1H).
Mass (m/z): 217.2 (M–H)$^-$
LC-MS (% Area Method): 97.79%

Scheme 1

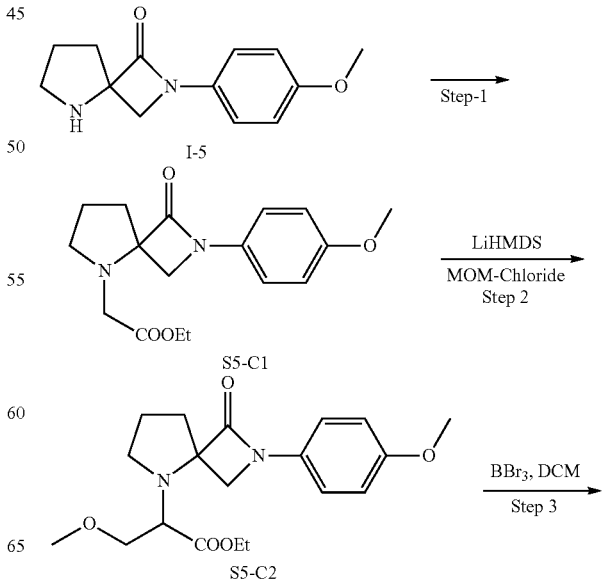

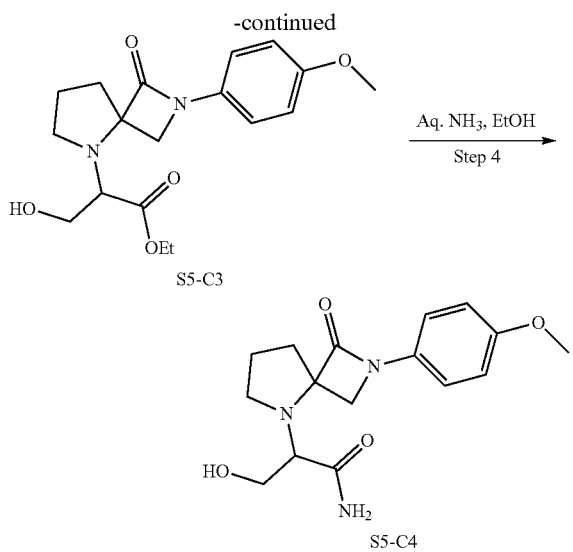

Step-1

Synthesis of Ethyl 2-(2-(4-methoxyphenyl)-1-oxo-2, 5-diazaspiro [3,4] octan-5-yl) acetate Referring to Scheme 1, to a solution of I-5 (160 mg, 0.698 mmoles) in acetonitrile (5 mL) was added potassium carbonate (571 mg, 4.19 mmoles) and bromo ethyl acetate (0.11 mL, 1.05 mmoles) and the resulting reaction mixture was heated to 70° C. for 12 h. After the completion of reaction the reaction was filtered through celite bed and filtrate was concentrated under reduced pressure to get crude compound. The crude compound was purified by column chromatography (100-200 mesh silica gel, 40% EtOAe in hexane) to give S5-C1 (130 mg, yield 60%) as a brown liquid.

TLC system: 50% EtOAc-Hexane
Rf-value: 0.3
Visualization: UV & phosphomolybdic acid stain
Analytical Data:
$^1$H NMR (400 MHz, CDCl$_3$): δ7.31 (d, 2H), 7.30 (d, 2H), 6.87 (d, 2H), 4.26 (q, 2H), 3.79 (s, 3H), 3.69 (s, 1H), 3.63 (m, 1H), 3.53 (d, 1H), 3.36-3.34 (m, 1H), 2.88 (q, 1H), 2.40-2.34 (m, 1H), 2.26-2.4 (m, 1H), 2.03-1.97 (m, 1H), 1.29-1.24 (m, 3H).
Mass (m/z): 319.2 (M−H)$^−$
LC-MS (% Area Method): 90.13%

Step 2

Synthesis of ethyl 2-methoxy-2-(2-(4-methoxyphenyl)-1-oxo-2,5-diazaspiro[3,4]octan-5-yl)acetate A stirred solution of S5-C1 (75 mg, 0.23 mmoles) in tetrahydrofuran (2 mL) at rt under nitrogen atmosphere was cooled to −40° C. LiHMDS (0.35 mL, 0.35 mmoles) was added to the reaction mixture and stirred for 40 min at −40° C. MOM chloride (0.075 mL, 0.46 mmoles) was added drop wise to the reaction and stirred for 10 min at −40° C. The resulting reaction mixture was allowed to stir at rt for 12 h. After the completion of reaction, the reaction mixture was quenched with saturated ammonium chloride and extracted with ethyl acetate. The combined organic layers were washed with water, brine solution and dried over anhydrous Na$_2$SO$_4$ and concentrated under vacuum to obtain the crude product which was purified by column chromatography (100-200 mesh silica gel, 25% EtOAc in hexane) to give S5-C2 (10 mg, yield: 35%) as an light yellow liquid.

TLC system: 50% EtOAc-Hexane
Rf-value: 0.4
Visualization: UV & Ninhydrin
Analytical Data:
$^1$H NMR (400 MHz, CDCl$_3$): δ7.30 (d, 2H), 6.86 (d, 2H), 4.19-4.16 (m, 2H), 3.88 (m, 1H), 3.77 (s, 3H), 3.74-3.71 (m, 3H), 3.64 (m, 1H), 3.52 (m, 1H), 3.33 (m, 2H), 3.28-3.21 (m, 1H), 3.11-3.07 (m, 1H), 2.38-2.30 (m, 1H), 2.14-2.09 (m, 1H), 1.99-1.82 (m, 2H), 1.22 (3H).
Mass (m/z): 362.7 (M)$^+$
LC-MS (% Area Method): 85.8% (RT 10.7 min)

Step 3

To a solution of S5-C2 (100 mg, 0.276 mmoles) in dry DCM (2 mL) was added boron tribromide (1.3 mL) at −78° C. and stirring continued for 4 h. After the completion of starting compound, the reaction was quenched with aq. sat. sodium bicarbonate and extracted with DCM, (2×10 mL). The combined organic layers were washed with brine solution and dried over anhydrous Na$_2$SO$_4$ and concentrated under vacuum to get crude. The crude reaction mixture was purified by column chromatography (100-200 mesh silica gel, 40% EtOAc in hexane) to give S5-C3 (20 mg, yield: 9.6%) as a colorless syrup.

TLC system: 50% EtOAc-Hexane. Rf-value: 0.3
Visualization: UV
Analytical Data:
$^1$H NMR (400 MHz, CDCl$_3$): δ7.35 (d, 2H, J=8.8 Hz), 6.89 (d, 2H, J=8.8 Hz), 4.19 (m, 2H), 3.82 (m, 1H), 3.72-3.89 (m, 5H), 3.67 (d, 1H), 3.19 (m, 1H), 2.98 (m, 1H), 2.45 (m, 1H), 2.20 (m, 1H), 2.01 (m, 2H), 1.29 (m, 2H), 1.32 (t, 3H).
Mass (m/z): 348.7 (M)$^+$
LC-MS (% Area Method): 90% (RT: 8.8 min and 9.4 min; diastereomers)

Step 4

To a solution of S5-C3 (40 mg, 0.11 mmoles) in ethanol (2 mL) aq. ammonia (2 mL) was added at 0° C., and stirred for 12 h at rt. After the completion of starting material, the reaction mixture was diluted with DCM (25 mL) and washed with water (2×15 mL). The combined organic layers were washed with brine solution and dried over anhydrous Na$_2$SO$_4$. The solvent was evaporated under vacuum to obtain crude product, which was purified by column chromatography (100-200 mesh silica gel, 2% MeOH in DCM) to give S5-C4 (12 mg, yield 33%) as a colorless gummy solid.

TLC system: 10% MeOH in DCM. Rf-value: 0.2
Visualization: UV
Analytical Data:
$^1$H NMR (400 MHz, CDCl$_3$): δ7.63 (br s, 1H), 7.18 (d, 2H), 6.90 (d, 2H), 5.80 (s, 1H), 4.23 (m, 1H), 3.98 (m, 2H), 3.86 (m, 2H), 3.80 (s, 3H), 3.62 (m, 1H), 3.21 (m, 11H), 2.72 (m, 1H), 2.40 (m, 1H), 1.80 (m, 2H), 1.68 (m, 1H).
Mass (m/z): 319.7 (M)$^+$

Scheme 2

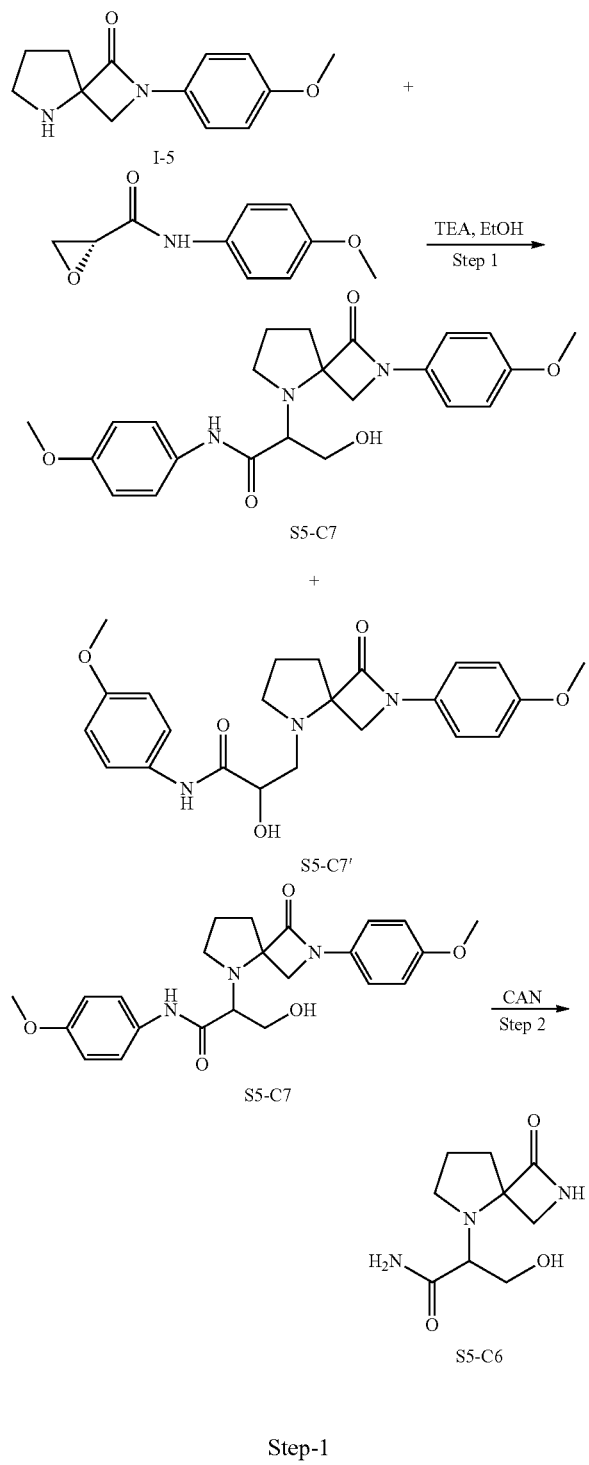

Step-1

Synthesis of 2-hydroxy-N-(4-methoxyphenyl)-3-(2-(4-methoxyphenyl)-1-oxo-2,5-diazaspiro[3.4]octan-5-yl)propionamide & 3-hydroxy-N-(4-methoxyphenyl)-2-(2-(4-methoxyphenyl)-1-oxo-2,5-diazaspiro[3,4]octan-5-yl)propionamide Referring to Scheme 2, to a mixture of I-5 (300 mg, 1.29 mmoles), (R)—N-(4-methoxyphenyl)oxirane-2-carboxamide (275 mg, 1.42 mmoles) and triethyl amine (0.3 mL, 5.16 mmoles) in ethanol (30 mL) was heated using microwave for 10 min at 800 W (1 min×10 times). After the completion of reaction, the reaction was concentrated under reduced pressure to get crude. The crude material was purified by Prep HPLC to give S5-C7 (70 mg, 30%) and S5-C7' (75 mg, 33%) as a brown syrup.

TLC system: 10% Methanol-DCM
Rf-value: 0.4
Visualization: UV & phosphomolybdic acid stain
Analytical data: C-5:
$^1$H NMR (400 MHz, CDCl$_3$): δ8.85 (s, 1H), 7.51 (d, 2H), 7.30 (d, 2H), 6.86 (m, 4H), 4.18 (t, 1H), 3.80 (s, 1H), 3.78 (s, 6H), 3.74 (d, 1H), 3.54 (d, 1H), 3.21 (m, 1H), 3.19-3.16 (m, 2H), 2.90 (m, 1H), 2.42 (q, 1H), 2.20-2.17 (m, 1H), 2.03-1.95 (m, 1H), 1.92 (m, 1H).
Mass (m/z): 425.5 (M)$^+$
HPLC (% Area Method): 93.7%
Analytical data: C-5':
$^1$H NMR (400 MHz, CDCl$_3$): δ8.95 (s, 1H), 7.45 (d, 2H), 7.30 (d, 2H), 6.92-6.85 (m, 4H), 4.80 (dd, 1H), 4.16 (m, 2H), 3.96 (s, 1H), 3.88 (dd, 1H), 3.81 (s, 3H), 3.78 (s, 3H), 3.48 (q, 1H), 3.36 (q, 1H), 2.68-2.58 (m, 1H), 2.56-2.47 (m, 1H), 2.42-2.30 (m, 1H), 2.18-2.11 (m, 1H).
Mass (m/z): 425.6 (M)$^-$
HPLC (% Area Method): 98.25%

Step 2

Synthesis of 3-hydroxy-2-(1-oxo-2, 5-diazaspiro [3,4] octan-5-yl) propionamide

To a solution of S5-C7 (30 mg, 0.070 mmoles) in acetonitrile and water (3 mL, 2:1) was added cerric ammonium nitrate (154 mg, 0.352 mmoles) at 0° C. and stirred for another 3 h at 0° C. After completion of reaction, acetonitrile was evaporated under reduced pressure and diluted with water (15 mL). The aqueous layer was washed with ethyl acetate to remove impurities. Evaporation of the aq. layer under reduced pressure gave the crude product which was purified by column chromatography (100-200 mesh silica gel, 2-8% Methanol in DCM) to give S5-C6 (10 mg, yield: 66%) as a light yellow gummy solid.

TLC system: 100% EtOAc
Rf-value: 0.1
Visualization: Phosphomolybdic acid stain
Analytical Data:
Mass (m/z): 214.7 (M–H)$^+$
$^1$H NMR (400 MHz, D$_2$O): ** Broad peak shapes were observed in D$_2$O

Scheme 3

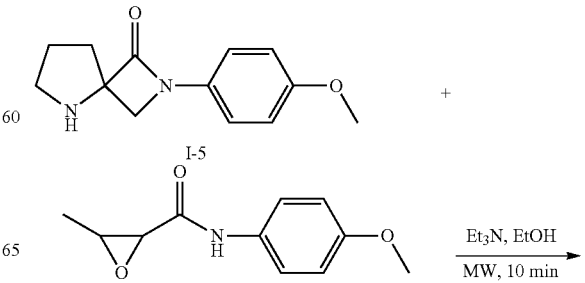

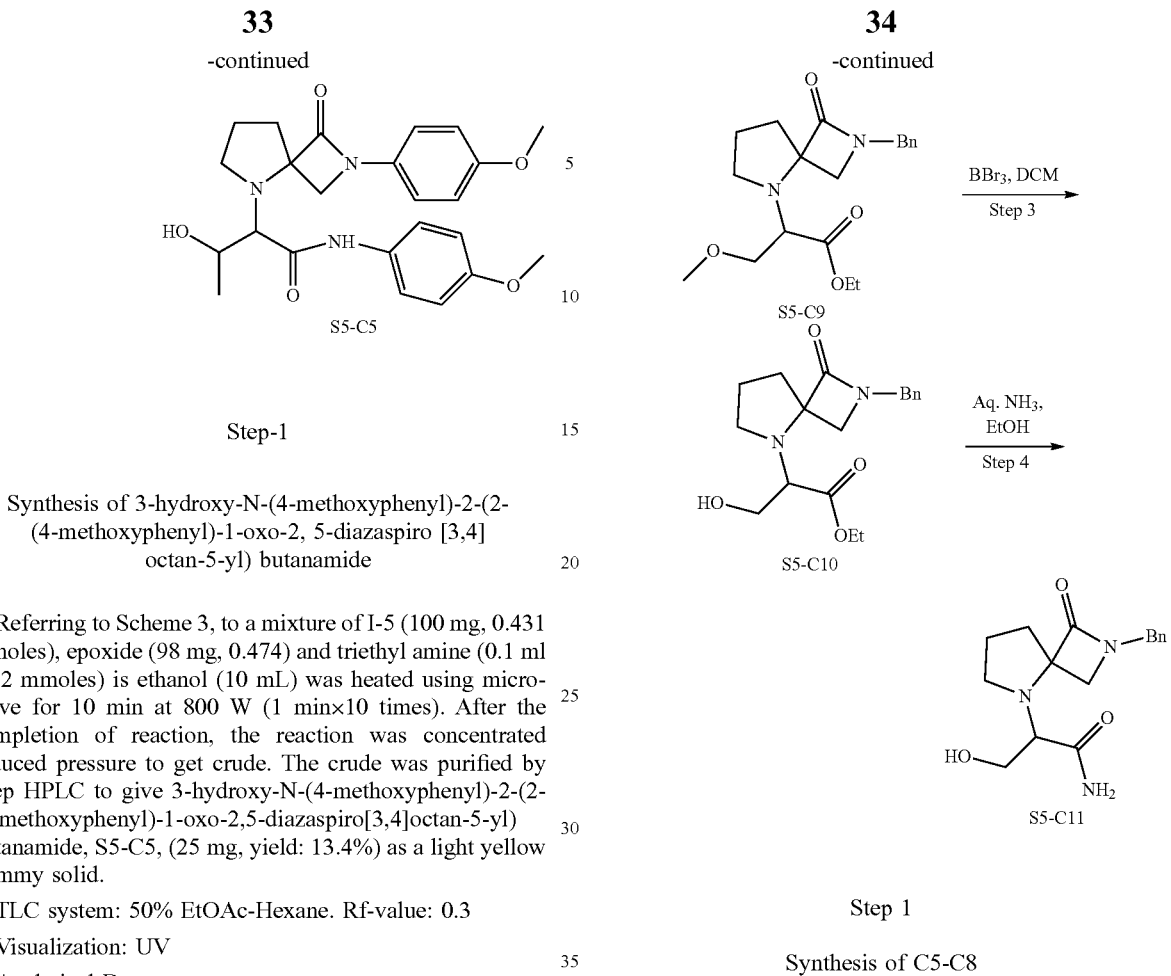

Step-1

Synthesis of 3-hydroxy-N-(4-methoxyphenyl)-2-(2-(4-methoxyphenyl)-1-oxo-2, 5-diazaspiro [3,4] octan-5-yl) butanamide Referring to Scheme 3, to a mixture of I-5 (100 mg, 0.431 mmoles), epoxide (98 mg, 0.474) and triethyl amine (0.1 ml 1.72 mmoles) is ethanol (10 mL) was heated using microwave for 10 min at 800 W (1 min×10 times). After the completion of reaction, the reaction was concentrated reduced pressure to get crude. The crude was purified by Prep HPLC to give 3-hydroxy-N-(4-methoxyphenyl)-2-(2-(4-methoxyphenyl)-1-oxo-2,5-diazaspiro[3,4]octan-5-yl) butanamide, S5-C5, (25 mg, yield: 13.4%) as a light yellow gummy solid.

TLC system: 50% EtOAc-Hexane. Rf-value: 0.3

Visualization: UV

Analytical Data:

$^1$H NMR (400 MHz, CDCl$_3$): δ9.30 (s, 1H), 7.44 (d, 2H), 7.27 (d, 2H), 6.87 (d, 4H), 4.15 (m, 1H), 3.80 (s, 6H), 3.79 (s, 1H), 3.61 (s, 1H), 3.37 (m, 1H), 3.26 (q, 1H), 3.02 (m, 1H), 2.43 (q, 1H), 2.23 (m, 2H), 2.07-2.05 (m, 1H), 2.02-1.96 (m, 1H), 1.37 (d, 3H).

Mass (m/z): 439.5 (M)$^+$

LC-MS (% Area Method): 91.30%

Scheme 4

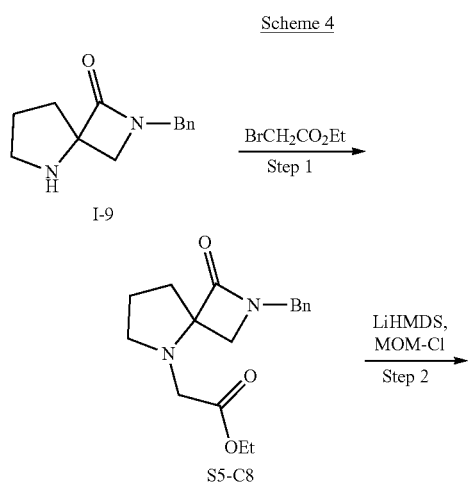

Step 1

Synthesis of C5-C8

Referring to Scheme 4, anhydrous K$_2$CO$_3$ (2.3 g, 16.6 mmoles) was added to a stirred solution of I-9 (600 mg, 2.77 mmoles) and ethylbromoacetate (0.46 mL, 4.16 mmoles) in acetonitrile (10 mL). The resulting mixture was heated at 65° C. for 12 h, then cooled to ambient temperature and filtered. The residue was washed with acetonitrile (2×10 mL), and combined of organic layers evaporated in vacuo. The residue was dissolved in EtOAc (25 mL), the solution was washed was washed with water (2×15 mL), brine, dried over Na$_2$SO$_4$, filtered, volatiles was evaporated in vacuo, and the residue subjected to the column chromatography on silica gel (100-200 mesh) using 30% EtOAc in hexanes as eluant to afford S5-C8 (640 mg, yield 76%) pale yellow syrup.

TLC system: 50% EtOAc in Hexanes

Rf-value: 0.4

Visualization: UV & minhydrin stain

LNB No: COS-13-A006-45

Analytical Data:

$^1$H NMR (400 MHz, CDCl$_3$): δ7.37 (m, 3H), 7.23 (m, 2H), 4.37 (s, 2H), 4.17 (q, 2H), 3.45 (s, 3.28 m, 1H), 3.22 (d, 1H), 3.15 (d, 1H), 2.84 (q, 1H), 2.28-2.26 (m, 1H), 2.09 (m, 1H), 1.96-1.89 (m, 2H), 1.24 (t, 3H).

Mass (m/z): 302.7 (M)$^+$

Step 2

Synthesis of S5-C9

To a solution of S5-C8 (100 mg, 0.331 mmoles) in dry tetrahydrofuran (5 mL) cooled to −78° C.; was added LiHMDS (0.66 mL) and stirred for 45 min. MOM-Cl (0.018 mL) was added dropwise to the reaction mixture and stirred for 2 h at −78° C. and, 12 h at room temperature. After the completion of reaction, the reaction mixture was quenched with sat ammonium chloride. The aqueous layer was extracted with ethyl acetate (2×10 mL). The combined organic layers were washed with brine solution and dried over anhydrous $Na_2SO_4$ and concentrated under vacuum to get crude product. Which was purified by column chromatography (100-200 mesh silica gel, 30% EtOAc in hexane) to give S5-C9 (20 mg, yield: 22%) as colorless syrup.

TLC system: 50% EtOAc-Hexane. Rf-value: 0.45
Visualization: UV
Analytical Data:
$^1$H NMR (400 MHz, $CDCl_3$): δ7.36-7.25 (m, 5H), 4.40-4.39 (d, 2H, J=4.8 Hz), 4.21-4.19 (d, 2H, J=3.84 (m, 1H), 3.76 (m, 1H), 3.64 (m, 1H), 3.36 (s, 3H), 3.29 (m, 1H), 3.19 (m, 1H), 3.18-3.11 (m, 1H), 3.02 (m, 1H), 2.32 (m, 1H), 2.06 (m, 1H), 1.88-1.75 (m, 2H), 1.22 (t, 3H, J=8 Hz)
Mass (m/z): 346.7 $(M)^+$
LC-MS (% Area Method): 89.31% (RT: 10.4 min)

Step 3

To a solution of S5-C9 (60 mg, 0.173 mmoles) in dry DCM (2 mL) was added boron tribromide (1.72 mL) at −78° C. and stirred at −78° C. for 12 h. After the completion of reaction, the reaction was quenched with sat. sodium bicarbonate and extracted with DCM (2×10 mL). The combined organic layers were washed with brine solution and dried over anhydrous $Na_2SO_4$ and concentrated under vacuum to get crude. The crude reaction mixture was purified by column chromatography (100-200 mesh silica gel, 50% EtOAc in hexane) to give S5-C10 (13 mg, yield: 23%) as colorless syrup.

TLC system: 50% EtOAc-Hexane. Rf-value: 0.3
Visualization: UV
Analytical Data:
$^1$H NMR (400 MHz, $CDCl_3$): δ7.37-7.24 (m, 10H), 4.44-4.40 (m, 2H), 4.29 (m, 2H), 4.21-4.19 (m, 2H), 4.08 (m, 2H), 3.89 (n, 1H), 3.85, (m, 1H), 3.69 (m, 1H), 3.65-3.63 (m, 3H), 3.36-3.34 (m, 2H), 3.22-3.21 (m, 1H), 3.14-3.10 (m, 5H), 3.09 (m, 1H), 2.39 (m, 2H), 2.12-1.75 (m, 5H), 1.99-1.89 (m, 2H), 1.31-1.27 (m, 3H, J=16 Hz), 1.22-1.19 (t, 3H, J=12 Hz).
Mass (m/z): 332.70 $(M)^+$
LC-MS (% Area Method): 96.2.1% (RT: 8.6 min and 9.4 min)

Step 4

To a solution of S5-C10 (100 mg, 0.301 mmoles) in ethanol (4 mL) and added at ammonia was added and stirred for 12 h at rt. After the completion of reaction, the reaction was diluted with DCM (25 mL) and washed with water (2×15 mL). The combined organic layers were washed with brine solution and dried over anhydrous $Na_2SO_4$ and concentrated under vacuum to get the crude product, which was purified by column chromatography (100-200 mesh silica gel, 2% MeOH in DCM) to give S5-C11 (60 mg, 66%) as colorless syrup.

TLC system: 10% MeOH in DCM. Rf-value: 0.4
Visualization: UV
Analytical Data:
$^1$H NMR (400 MHz, $CDCl_3$): δ7.53 (br s, 1H), 7.35-7.28 (m, 5H), 5.51 (br s, 1H), 4.72-4.68 (d, 1H, J=16 Hz), 4.48-4.45 (d, 1H, J=12 Hz), 4.14 (m, 1H), 3.87 (m, 1H), 3.56-3.52 (d, 1H, J=16 Hz), 3.47 (m, 1H), 3.41-3.37 (d, 1H, J=16 Hz), 3.20 (br s, 1H), 3.06 (m, 1H), 2.50 (m, 1H), 2.15 (m, 1H), 1.59-1.56 (m, 2H), 1.25 (m, 1H).
Mass (m/z): 303.7 $(M)^+$

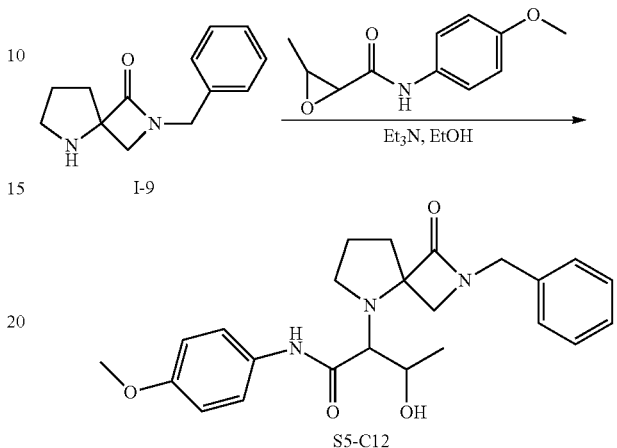

Scheme 5

Step-1

Synthesis of 2-(2-benzyl-1-oxo-2,5-diazaspiro[3,4]octan-5-yl)-3-hydroxy-N-(4-methoxyphenyl)butanamide Referring to Scheme 5, to a mixture of I-9 (200 mg, 0.925 mmoles), epoxide (175 mg, 1.01) and triethyl amine (0.43 mL) in ethanol (10 mL) was irradiated to micro waves for 10-12 min at 800 W min×12 times). After the completion of reaction, the reaction was concentrated reduced pressure to get crude mixture. The crude was purified by column chromatography (100-200 mesh silica gel, 60-70% EtOAc in Hexane) to give 2-(2-benzyl-1-oxo-2,5-diazaspiro[3,4]octan-5-yl)-3-hydroxy-N-(4-methoxyphenyl)butanamide, S5-C12, (15 mg, 4%) as a colorless gummy syrup.

TLC system: EtOAc Rf-value: 0.4
Visualization: UV
Analytical Data:
$^1$H NMR (400 MHz, $CDCl_3$): δ9.33 (s, 1H), 7.40 (t, 2H), 7.35-7.29 (m, 3H), 7.19 (d, 2H), 6.85 (d, 2H), 4.42 (d, 1H), 4.31 (d, 1H), 4.10 (d, 1H), 3.78 (s, 3H), 3.27 (d, 1H), 3.23-3.15 (m, 2H), 3.08 (d, 1H), 2.90 (d, 1H), 2.36-2.30 (m, 1H), 2.09-2.03 (m, 1H), 1.99 (m, 2H), 1.87-1.83 (m, 1H), 1.31 (d, 3H).
Mass (m/z): 424.30 $(M+H)^+$
LC-MS (% Area Method): 95.31% (RT: 9.9 min)

Example 2—[$^3$H] MK-801 Binding Assay

Methods

Assays were conducted as described in Moskal et al. (Moskal, J. R., Kuo, A. G., Weiss, C., Wood, P. L., O'Connor Hanson, A., Kelso, S., Harris, R. B., Disterhoft, S. F., 2005. GLYX-13: a monoclonal antibody-derived peptide that acts as an N-methyl-D-aspartate receptor modulator. Neuropharmacology. 49, 1077-87) The potentiation of [$^3$H]MK-801 binding (5 nM; 22.5 Ci/mmol) to well washed rat cortical membranes (200 μg) was measured under non-equilibrium conditions (15 min @25° C.) in the presence of increasing concentrations of test compounds and 50 μM glutamate. Zero levels were determined in the absence of any glycine ligand and in the presence of 30 μM 5.7 DCKA. Maximal stimulation was measured in the presence of 1 mM glycine, and 50 μM glutamate was present in all samples. The facilitation of [$^3$H]MK-801 binding by tests compounds was calculated by using a 3 parameter log agonist vs. response equation (Graph pad Prism, USA) and potency (EC$_{50}$, expressed in pM) and maximal activity (% maximal stimulation) were calculated for the test compound. Data for compound Z is provided in Table 2 below.

TABLE 2

| Compound | MK-801 Glycine Site Binding Assay: Rat, Cortex EC50 (M) | LTP: LTP Augmentation (%) | LTP: LTP Concentration (uM) | LTP: LTP Significance, S or NS |
|---|---|---|---|---|
| X | 2.43E−09 | 75 | 1 | NS |

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:
1. A compound represented by formula I:

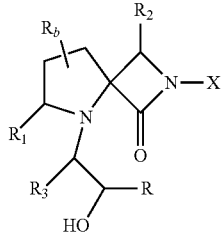

(I)

or a stereoisomer, an N-oxide, and/or a pharmaceutically acceptable salt thereof, wherein
R$_b$ is H;
R is H or C$_1$-C$_6$ alkyl;
R$_1$ is H;
R$_2$ is H;
R$_3$ is —CONR'R', wherein R' for each occurrence is independently selected from H, tert-butoxycarbonyl, carbobenzyloxycarbonyl, p-methoxybenzyloxycarbonyl, acetyl, trifluoroacetyl, benzoyl, benzyl, p-methoxybenzyl, p-methoxyphenyl, 3,4-dimethoxybenzyl, triphenylmethyl, and p-toluenesulfonyl; and
X is H, X', —C$_1$-C$_6$ alkylene-X', or —C$_1$-C$_6$ alkylene-C(O)—X', wherein X' is selected from the group consisting of:

(i) heterocyclyl including from 3 to 6 ring atoms wherein 1, 2, or 3 of the ring atoms are independently selected from the group consisting of N and O; and
(ii) phenyl;
wherein X' is optionally substituted by one or more substituents independently selected from the group consisting of hydroxyl and C$_1$-C$_6$ alkoxy.
2. The compound of claim 1, wherein R is H.
3. The compound of claim 1, wherein R is methyl.
4. The compound of claim 1, wherein one of R' is H and the other R' is p-methoxyphenyl.
5. The compound of claim 1, wherein each of R' is H.
6. The compound of claim 1, wherein X is H.
7. The compound of claim 1, wherein X is X'.
8. The compound of claim 1, wherein X is p-methoxyphenyl.
9. The compound of claim 1, wherein X is —C$_1$-C$_6$ alkylene-X'.
10. The compound of claim 1, wherein X is benzyl.
11. The compound of claim 1, wherein X is —C$_1$-C$_6$ alkylene-C(O)—X'.
12. The compound of claim 1, wherein X is

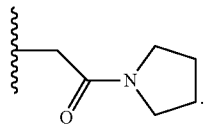 [SMILES: *CC(=O)N1CCCC1]

13. A method of treating neuropathic pain, the method comprising:
administering to a patient in need thereof a compound represented by formula (I):

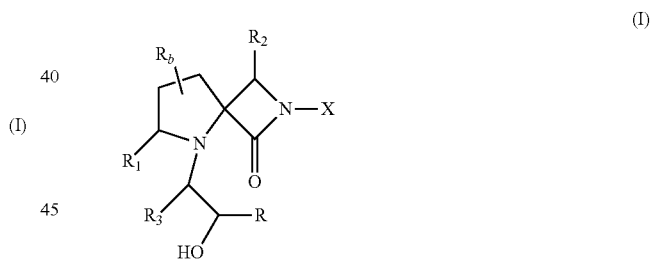

(I)

or a stereoisomer, or an N-oxide, and/or a pharmaceutically acceptable salt thereof, wherein:
R$_b$ is selected from the group consisting of H, halogen, hydroxyl, cyano and C$_1$-C$_6$ alkyl;
R is H or C$_1$-C$_6$ alkyl;
R$_1$ is H or C$_1$-C$_6$ alkyl;
R$_2$ is H or C$_1$-C$_6$ alkyl;
R$_3$ is selected from the group consisting of H, C$_1$-C$_6$ alkyl, —OH, C$_1$-C$_6$ alkoxy, —CO$_2$H, and —CONR'R', wherein R' for each occurrence is independently selected from H, C$_1$-C$_6$ alkyl, 9-fluorenylmethyloxycarbonyl, tert-butoxycarbonyl, carbobenzyloxycarbonyl, p-methoxybenzyloxycarbonyl, acetyl, trifluoroacetyl, benzoyl, benzyl, p-methoxybenzyl, p-methoxyphenyl, 3,4-dimethoxybenzyl, triphenylmethyl, p-toluenesulfonyl, —C(O)OR$_{31}$ and —C(O)R$_{32}$, wherein
R$_{31}$ is selected from the group consisting of C$_1$-C$_6$ alkyl, C$_1$-C$_6$ haloalkyl, C$_2$-C$_6$ alkenyl, C$_2$-C$_6$ alkynyl, $C_3$-$C_{10}$ cycloalkyl, —$CH_2$—$C_3$-$C_{10}$ cycloalkyl, —$CH_2$-phenyl, and —$CH_2$-pyridyl, wherein the $C_3$-$C_{10}$ cycloalkyl is optionally substituted with from 1-3 independently selected $C_1$-$C_3$ alkyl; and the phenyl is optionally substituted with from 1-2 substituents independently selected from $C_1$-$C_3$ alkyl, $C_1$-$C_3$ haloalkyl, $C_1$-$C_3$ alkoxy, $C_1$-$C_3$ haloalkoxy, nitro, halo, $SO_2Me$, cyano, and —OC(O)$CH_3$; and $R_{32}$ is selected from the group consisting of H, $C_1$-$C_6$ alkyl, $C_1$-$C_6$ haloalkyl, phenyl, and pyridyl, wherein the phenyl is optionally substituted with from 1-2 substituents independently selected from $C_1$-$C_3$ alkyl, $C_1$-$C_3$ haloalkyl, $C_1$-$C_3$ alkoxy, $C_1$-$C_3$ haloalkoxy, nitro, halo, $SO_2Me$, cyano, and —OC(O)$CH_3$; and X is H, X', —$C_1$-$C_6$ alkylene-X', or —$C_1$-$C_6$ alkylene-C(O)—X', wherein X' is selected from the group consisting of:
(i) $C_3$-$C_6$ cycloalkyl;
(ii) heterocyclyl including from 3 to 6 ring atoms wherein 1, 2, or 3 of the ring atoms are independently selected from the group consisting of N, O, and S;
(iii) phenyl; and
(iv) heteroaryl including from 5 to 6 ring atoms wherein 1, 2, or 3 of the ring atoms are independently selected from the group consisting of N, O, and S;
wherein X' is optionally substituted by one or more substituents independently selected from the group consisting of halogen, hydroxyl, $C_1$-$C_6$ alkyl and $C_1$-$C_6$ alkoxy.

14. The method of claim 13, wherein $R_b$ is H; R is H or methyl; $R_1$ is H; $R_2$ is H; $R^3$ is —CONR'R'; one of R' is H; and X is H.

15. The method of claim 13, wherein $R_b$ is H; R is H or methyl; $R_1$ is H; $R_2$ is H; $R^3$ is —CONR'R'; one of R' is H; and X is benzyl, p-methoxyphenyl, or

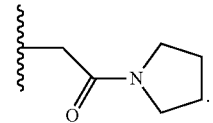 [SMILES: *CC(=O)N1CCCC1]

16. The method of claim 13, wherein the neuropathic pain is acute.

17. The method of claim 13, wherein the neuropathic pain is chronic.

18. The method of claim 13, wherein the neuropathic pain is associated with fibromyalgia.

19. The method of claim 13, wherein the neuropathic pain is associated with diabetic neuropathy.

20. The method of claim 13, wherein the neuropathic pain is associated with herpes, HIV, traumatic nerve injury, stroke, post-ischemia, reflex sympathetic dystrophy, complex regional pain syndrome, spinal cord injury, sciatica, phantom limb pain, or cancer chemotherapeutic-induced neuropathic pain.

* * * * *